(12) United States Patent
Hee-Hanson et al.

(10) Patent No.: US 12,274,871 B1
(45) Date of Patent: Apr. 15, 2025

(54) HOLD DETENT MECHANISM FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/619,996

(22) Filed: Mar. 28, 2024

(51) Int. Cl.
*A61M 5/32* (2006.01)
*A61M 5/24* (2006.01)

(52) U.S. Cl.
CPC ................... *A61M 5/322* (2013.01)

(58) Field of Classification Search
CPC ................ A61M 5/326; A61M 5/3243; A61M 2005/3247
See application file for complete search history.

(56) References Cited

U.S. PATENT DOCUMENTS

| | | |
|---|---|---|
| 4,900,311 A | 2/1990 | Stern et al. |
| 5,088,986 A | 2/1992 | Nusbaum |
| 5,290,256 A | 3/1994 | Weatherford et al. |
| 5,688,241 A * | 11/1997 | Asbaghi .............. A61M 5/3272 604/110 |
| 7,597,685 B2 | 10/2009 | Olson |
| 8,016,797 B2 | 9/2011 | Gratwohl et al. |
| 8,821,451 B2 | 9/2014 | Daniel |
| 9,199,038 B2 | 12/2015 | Daniel |
| 9,408,976 B2 | 8/2016 | Olson et al. |
| 9,498,579 B2 | 11/2016 | Ruan |

(Continued)

FOREIGN PATENT DOCUMENTS

WO   WO 2011/123024       10/2011
WO   WO 2014/115241 A1    7/2014

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

Some injection devices include an injection device body, a needle shroud retractable into the injection device body, a control spring coupled to the needle shroud and biased to cause the needle shroud to be at least partially extended from the injection device body in an initial position, and a hold detent mechanism coupled to at least the needle shroud. The hold detent mechanism is configured to (i) activate, when the needle shroud is retracted from the initial position into the injection device body to a hold position, to create a hold detent force, and (ii) deactivate, when the needle shroud is extracted from the hold position subsequent to the retraction, to release the hold detent force and enable the needle shroud to extend from the injection device body to substantially the initial position.

27 Claims, 13 Drawing Sheets

(56) References Cited

U.S. PATENT DOCUMENTS

| | | |
|---|---|---|
| 9,662,452 B2 | 5/2017 | Daniel |
| 9,867,940 B2 | 1/2018 | Holmqvist et al. |
| 9,919,107 B2 * | 3/2018 | Imai .................... A61M 5/326 |
| 10,420,898 B2 | 9/2019 | Daniel |
| 11,369,751 B2 * | 6/2022 | Ruan ................... A61M 5/3272 |
| 11,944,787 B2 | 4/2024 | Franke |
| 2006/0276756 A1 | 12/2006 | Francavilla |
| 2010/0268170 A1 | 10/2010 | Carrel et al. |
| 2012/0203186 A1 | 8/2012 | Vogt et al. |
| 2013/0041328 A1 | 2/2013 | Daniel |
| 2013/0096512 A1 | 4/2013 | Ekan et al. |
| 2013/0123710 A1 | 5/2013 | Ekman et al. |
| 2013/0261559 A1 | 10/2013 | Werbickas |
| 2014/0025013 A1 | 1/2014 | Dowds et al. |
| 2015/0190580 A1 | 7/2015 | Imai et al. |
| 2015/0258283 A1 | 9/2015 | Imai et al. |
| 2016/0089498 A1 | 3/2016 | Daniel |
| 2018/0064875 A1 | 3/2018 | Holmqvist |
| 2018/0361082 A1 | 12/2018 | Sall et al. |
| 2020/0289755 A1 | 9/2020 | Franke |
| 2021/0236732 A1 | 8/2021 | Chu et al. |
| 2021/0244887 A1 | 8/2021 | Halseth |
| 2021/0393886 A1 | 12/2021 | Nicolas et al. |
| 2022/0387719 A1 | 12/2022 | Wang et al. |
| 2022/0395642 A1 | 12/2022 | Karlsson |
| 2024/0139430 A1 | 5/2024 | Chansavang et al. |
| 2024/0165346 A1 | 5/2024 | Chansavang et al. |

FOREIGN PATENT DOCUMENTS

| | | |
|---|---|---|
| WO | WO 2021/008839 | 1/2021 |
| WO | WO 2023/104512 A1 | 6/2023 |

OTHER PUBLICATIONS

U.S. Appl. No. 18/619,754, filed Mar. 28, 2024, Alexander Hee-Hanson.

U.S. Appl. No. 18/619,991, filed Mar. 28, 2024, Alexander Hee-Hanson.

U.S. Appl. No. 18/620,210, filed Mar. 28, 2024, Alexander Hee-Hanson.

U.S. Appl. No. 18/620,586, filed Mar. 28, 2024, Alexander Hee-Hanson.

U.S. Appl. No. 18/620,097, filed Mar. 28, 2024, Alexander Hee-Hanson.

* cited by examiner

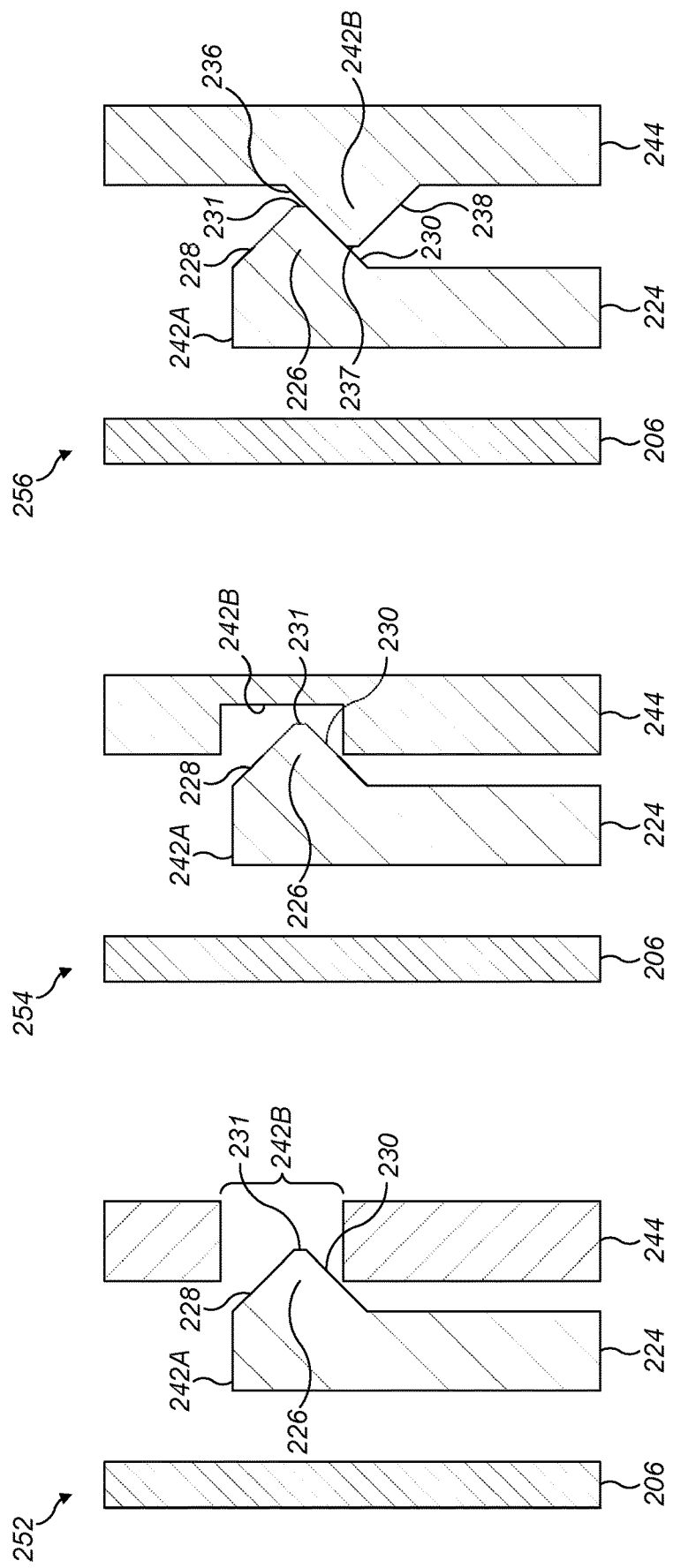

HOLD DETENT MECHANISM FOR INJECTION DEVICES

TECHNICAL FIELD

This application relates to an injector device for delivery of a medicament, particularly to an auto-injector device.

BACKGROUND

An auto-injector may be described as a device which completely or partially replaces the activities involved in parenteral drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle shroud/sleeve/cover which is biased by a spring (the control spring) to extend out of the device. On removal of the device from the injection site, this control spring automatically extends the needle shroud past the needle to provide needle shielding. On activation of the device, the needle shroud is pushed into the device. A user has to provide the force to actuate the needle shroud, overcome the activation mechanism forces, and compress the control spring (activation force). More importantly, during drug delivery the user holds the device at the injection site and apply a force (hold force) parallel to the needle shroud direction of extension to react the needle shroud biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This results in pain, discomfort, a wet injection site, early device removal and partial drug delivery.

SUMMARY

According to a first aspect of this disclosure, there is described an injection device comprising: an injection device body; a needle shroud retractable into the injection device body; a control spring coupled to the needle shroud and biased to cause the needle shroud to be at least partially extended from the injection device body in an initial position; and a hold detent mechanism coupled to at least the needle shroud, wherein the hold detent mechanism is configured to: activate, when the needle shroud is retracted from the initial position into the injection device body to a hold position, to create a hold detent force opposite a control spring force caused by compression of the control spring during said retraction of needle shroud to said hold position; and deactivate, when the needle shroud is extracted from the hold position subsequent to the retraction, to release the hold detent force and enable the needle shroud to extend from the injection device body to substantially the initial position.

The hold detent mechanism may comprise a first hold detent feature coupled to the needle shroud, which, when activated, interacts with a second hold detent feature on the injection device body for creating the hold detent force.

The injection device may further comprise a collar within the injection device body and configured for guiding said needle shroud between the initial position and the hold position, wherein the hold detent mechanism comprises a first hold detent feature coupled to the needle shroud, which, when activated, interacts with a second hold detent feature on the collar for creating the hold detent force.

The first hold detent feature may comprise at least one of: a flexible arm; a resilient clip; a high friction interface; partial cut-out or flap on the needle shroud; any other member or mechanism for creating a hold detent force opposite the control spring force caused by compression of the control spring during said retraction of needle shroud to said hold position.

The first hold detent feature may comprise a male feature and the second hold detent feature comprises at least one of: a recess for mating with said male feature of the first hold detent feature; a partial recess for mating with said male feature of the first hold detent feature; a male feature configured to interact and couple with the male feature of the first hold detent feature; a high friction interface; any other member or mechanism for interacting with the first hold detent feature for creating a hold detent force opposite the control spring force caused by compression of the control spring during said retraction of needle shroud to said hold position.

The male feature of the first hold detent feature may comprise at least one ramped contact face configured for flexing a portion of the first hold detent feature radially away from the injection device body or collar when the needle shroud is in the first position and/or prior retracting to the hold position; when the needle shroud is retracted to the hold position, the hold detent mechanism activates by the at least one ramped contact face of the male feature of the first hold detent feature interacting with the second hold detent feature of the injection device body or collar causing the portion of the first hold detent feature to radially flex towards the injection device body or collar, respectively, and create the hold detent force opposite the control spring force; and when the needle shroud is extracted from the hold position subsequent to the retraction, the hold detent mechanism is deactivated by the at least one ramped contact face of the male feature of the first hold detent feature interacting with the second hold detent feature to radially flex the portion of the first hold detent feature away from the injection device body or collar, respectively, enabling the control spring force to extract the needle shroud to substantially the first position.

The first hold detent feature may be coupled to the needle shroud by a snap fit.

The first hold detent feature may be integral to the needle shroud and formed by a resilient partial cut-out or flap of the needle shroud.

The hold detent force of the hold detent mechanism may at least partially support the needle shroud against the control spring force rather than the full control spring force being fully transferred to the user when the injection device is in the hold position.

The control spring may be a compression spring configured to bias the needle shroud towards an extended position.

The injection device may further comprise: a collar within the injection device body and rotatably configured for guiding said needle shroud between the initial position and the hold position; a plunger and biasing means for biasing the plunger towards the distal end of the injection device, wherein: when the needle shroud is in the initial position, the plunger is retained by a combination of the rear casing and the collar preventing the biasing means from displacing the plunger in the distal direction; and on activation of the injection device, the collar rotates and guides the needle shroud to the holding position and causing, when the needle shroud is in the holding position, the biasing means to move the plunger in the distal direction of the injection device.

The injection device may further comprise a needle, and wherein the needle shroud is arranged to shroud the needle when in an extended position.

The injection device may further comprise a reservoir containing a medicament, the reservoir coupled to the plunger via a stopper at a distal portion of the reservoir and the reservoir coupled to the needle at a proximal end of the reservoir, and wherein, when the needle shroud moves into the holding position, the biasing means moves the plunger to displace the stopper in the distal direction causing the medicament stored in the reservoir to be expelled from the injection device via the needle.

The injection device may further comprise at least two hold detent mechanisms equally spaced around the circumference of the needle shroud.

According to a second aspect of this disclosure, there is described a hold detent mechanism for an injection device, the hold detent mechanism comprising: a first hold detent feature coupled to a needle shroud, wherein the needle shroud is retractable into an injection device body and coupled to a control spring, the control spring biased to cause the needle shroud to be at least partially extended from the injection device body in an initial position; wherein the hold detent mechanism is configured to: activate the first hold detent feature, when the needle shroud is retracted from the initial position into the injection device body to a hold position, to create a hold detent force opposite a control spring force caused by compression of the control spring during said retraction of needle shroud to said hold position; and deactivate the first hold detent feature, when the needle shroud is extracted from the hold position subsequent to the retraction, to release the hold detent force and enable the needle shroud to extend from the injection device body to substantially the initial position.

The hold detent mechanism, wherein the first hold detent feature which, when activated, interacts with a second hold detent feature on the injection device body for creating the hold detent force.

The hold detent mechanism, wherein the injection device further comprises a collar within the injection device body and configured for guiding said needle shroud between the initial position and the hold position, wherein the first hold detent feature, which, when activated, interacts with a second hold detent feature on the collar for creating the hold detent force.

The hold detent mechanism, wherein the first hold detent feature comprises at least one of: a flexible arm; a resilient clip; a high friction interface; partial cut-out or flap on the needle shroud; any other member or mechanism for creating a hold detent force opposite the control spring force caused by compression of the control spring during said retraction of needle shroud to said hold position.

The hold detent mechanism, wherein the first hold detent feature comprises a male feature and the second hold detent feature comprises at least one of: a recess for mating with said male feature of the first hold detent feature; a partial recess for mating with said male feature of the first hold detent feature; a male feature configured to interact and couple with the male feature of the first hold detent feature; a high friction interface; any other member or mechanism for interacting with the first hold detent feature for creating a hold detent force opposite the control spring force caused by compression of the control spring during said retraction of needle shroud to said hold position.

The hold detent mechanism, wherein the male feature of the first hold detent feature comprises at least one ramped contact face configured for flexing a portion of the first hold detent feature radially away from the injection device body when the needle shroud is in the first position and/or prior retracting to the hold position; when the needle shroud is retracted to the hold position, the first hold detent feature of the hold detent mechanism activates by the at least one ramped contact face of the male feature of the first hold detent feature interacting with the second hold detent feature of the injection device body causing the portion of the first hold detent feature to radially flex towards the injection device body, respectively, and create the hold detent force opposite the control spring force; and when the needle shroud is extracted from the hold position subsequent to the retraction, the first hold detent feature of the hold detent mechanism is deactivated by the at least one ramped contact face of the male feature of the first hold detent feature interacting with the second hold detent feature to radially flex the portion of the first hold detent feature away from the injection device body, respectively, enabling the control spring force to extract the needle shroud to substantially the first position.

The hold detent mechanism, wherein the first hold detent feature comprises a male feature and the second hold detent feature comprises at least one of: a recess for mating with said male feature of the first hold detent feature; a partial recess for mating with said male feature of the first hold detent feature; a male feature configured to interact and couple with the male feature of the first hold detent feature; a high friction interface; any other member or mechanism for interacting with the first hold detent feature for creating a hold detent force opposite the control spring force caused by compression of the control spring during said retraction of needle shroud to said hold position.

The hold detent mechanism, wherein the male feature of the first hold detent feature comprises at least one ramped contact face configured for flexing a portion of the first hold detent feature radially away from the collar when the needle shroud is in the first position and/or prior retracting to the hold position; when the needle shroud is retracted to the hold position, the first hold detent feature of the hold detent mechanism activates by the at least one ramped contact face of the male feature of the first hold detent feature interacting with the second hold detent feature of the collar causing the portion of the first hold detent feature to radially flex towards the collar, respectively, and create the hold detent force opposite the control spring force; and when the needle shroud is extracted from the hold position subsequent to the retraction, the first hold detent feature of the hold detent mechanism is deactivated by the at least one ramped contact face of the male feature of the first hold detent feature interacting with the second hold detent feature to radially flex the portion of the first hold detent feature away from the collar, respectively, enabling the control spring force to extract the needle shroud to substantially the first position.

The hold detent mechanism, wherein the first hold detent feature is coupled to the needle shroud by a snap fit.

The hold detent mechanism, wherein the first hold detent feature is integral to the needle shroud and formed by a resilient partial cut-out of the needle shroud.

The hold detent mechanism, wherein the hold detent force of the hold detent mechanism at least be partially supports the needle shroud against the control spring force rather than the full control spring force being fully transferred to the user when the injection device is in the hold position.

The hold detent mechanism, wherein the control spring is a compression spring configured to bias the needle shroud towards an extended position.

According to a further aspect of this specification, there is described a method for reducing the holding force of a needle shroud of an injection device during use, the method comprising: during retraction of the needle shroud from an initial position into an injection device body, activating a hold detent mechanism coupled to the needle shroud when the needle shroud retracts to a hold position from the initial position, wherein the activated hold detent mechanism creates a hold detent force opposite a control spring force caused by compression of a control spring coupled to the needle shroud during said retraction of needle shroud to said hold position; during extension of the needle shroud from the hold position subsequent to the retraction to substantially the initial position, deactivating the hold detent mechanism when the needle shroud extends from the hold position to the initial position, wherein the deactivated hold detent mechanism releases the hold detent force and enables the needle shroud to extend from the injection device body to substantially the initial position; and subsequent to the extension of the needle shroud, preventing further retraction of the needle shroud into the injection device body using a locking mechanism.

Throughout this specification, use of the injection device is described in terms of a user, who operates the injection device, and a subject, who receives an injection from the injection device. The user and the subject may be the same person. Alternatively, the user and subject may be different entities, e.g., a healthcare provider and a patient or a vet/farmer and a pet/animal.

BRIEF DESCRIPTION OF THE DRAWINGS

Exemplary embodiments of the present disclosure are described with reference to the accompanying drawings, in which:

FIG. 2F shows a schematic example of a cross section of a hold detent mechanism for the injection device of FIG. 2E;

FIG. 2G shows a schematic example of a cross section of another hold detent mechanism for the injection device of FIG. 2E;

FIG. 2H shows a schematic example of a cross section of a further hold detent mechanism for the injection device of FIG. 2E;

DETAILED DESCRIPTION

Figure 1:
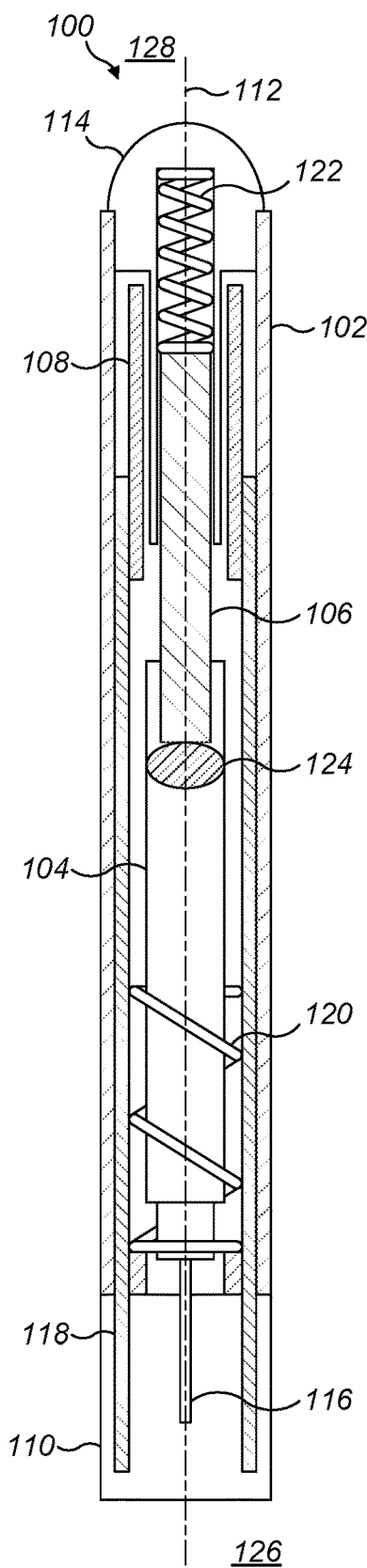
FIG. 1 shows a schematic example of a cross section of an injection device.

A drug delivery device, as described herein, may be configured to inject a medicament into a subject. For example, delivery could be sub-cutaneous, intra-muscular, or intravenous. Such a device could be operated by a subject or other user (e.g., a care-giver, nurse, or physician), and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml). The subject may include, without limitation, for example a person, a patient, a human, a mammal, a pet, farm animal, or animal and/or any other suitable subject that requires a dosage of a medicament delivered by the injection device. The subject may be, without limitation, for example the user or operator of the injection device (e.g., a person self-administering a medicament). The user or operator may include, without limitation, for example an operator of the device, a person, a care-giver, nurse, physician, vet, farmer, zookeeper, a robot or robotic arm or appendage configured for delivering a medicament via the injection device under remote control and/or automatic operation, a subject (e.g., user is the subject and self-administers the medicament via the injection device) and the like.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component.

Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors can require user actions to commence drug delivery. One of these actions apply an axial force to the device by either pushing a needle shroud/sleeve/cover into the device or pressing a button on the device. The axial force required is referred to as the activation force in this document. The magnitude and profile of this activation force and also, after activation, the magnitude and profile of the holding force required to hold the device at the injection site until the medicament is delivered has an impact on the usability of the device.

The user reacts to the control spring force during activation and when holding the device at the injection site. It may be beneficial to reduce the hold and/or activation force. Reducing the force to activate the needle shroud locking mechanism, enables a reduction in the control spring and therefore reduces the hold and activation forces. Moreover, reducing the force to hold the device and needle at the injection site while for delivering the medicament, reduces the energy or hold force required by a user and/or automatic holding mechanism in overcoming the opposing forces of the control spring and therefore reduces the hold forces required to operate the injection device. This can reduce the effort in applying the hold force during delivery of the medicament for the full drug delivery time, which may further reduce pain and/or discomfort for the subject and/or user while improving the correct working and operation of the injection device to ensure that the medicament is fully delivered to the subject.

After the device is removed from the user's body post use, many autoinjectors cover the needle with a needle shroud/needle cover, which is extended out of the device by a control spring. This needle shroud is locked in its extended position by a needle shroud locking mechanism, often featuring a one-way clip feature. The control spring has enough force to ensure this mechanism is activated following device removal.

Injection devices described herein use a hold detent mechanism for lowering the holding force to the user of the device for delivering the medicament. The injection device described herein comprises a hold detent mechanism that is coupled to at least the needle shroud of the injection device. For example, the hold detent mechanism may be coupled to the needle shroud and the outer casing or to the needle shroud and collar of the injection device, and/or both. The hold detent mechanism is configured to activate, when the needle shroud is retracted from the initial position into the injection device body to a hold position, to create a hold detent force opposite a control spring force caused by compression of the control spring during said retraction of needle shroud to said hold position. The hold detent mechanism is also configured to automatically deactivate, when the needle shroud is extracted from the hold position subsequent to the retraction, to release the hold detent force and enable the needle shroud to extend from the injection device body to substantially the initial position.

The force used to maintain the needle shroud in the hold position is less than the force required to maintain the hold position on many auto-injector needle shroud/cover mechanisms, resulting in a reduction in user hold force during delivery of the medicament to the subject.

FIG. 1 shows a schematic example of a cross section of an injection device 100. The injection device is configured to inject a medicament into a subject's body. The injection device 100 comprises an outer casing 102 that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically, a user removes cap 110 from the outer casing 102 before device 100 can be operated.

As shown, casing 102 is substantially cylindrical and has a substantially constant diameter along the longitudinal axis of the device 100. The injection device 100 has a distal region and a proximal region. The term "distal" refers to a location that is relatively closer to a site of injection, which is illustrated in FIG. 1 as distal end 126 of the injection device 100 or outer casing 102. The term "proximal" refers to a location that is relatively further away from the injection site, which is illustrated in FIG. 1 as proximal end 128 of the injection device 100 or typically the rear casing 114 from which the user may apply the activation and user hold forces.

The outer casing 102 is closed at a proximal end 128 by a rear casing 114. A needle 116 and a retractable needle shroud 118 (also referred to as a "needle sleeve" or "needle cover") extend from a distal end 126 of the outer casing 102. The retractable needle shroud 118 is biased in the distal direction of the injection device 100, for example using a control spring 120. The needle shroud 118 is coupled to the outer casing 102 to permit movement of needle shroud 118 relative to the outer casing 102. For example, the shroud 118 can move in a longitudinal direction parallel to longitudinal axis 112. Specifically, movement of shroud 118 in a proximal direction can permit a needle 116 to extend from the distal end 126 of the casing 102.

The plunger 106 is biased towards the distal end 126 of the injection device 100 by a biasing means, for example using a drive spring 122. The plunger 106 is retained in an initial position by a combination of the rear casing 114 and the collar 108, preventing the biasing means from displacing the plunger in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle shroud 118. Proximal movement of shroud 118 by placing a distal end of the shroud 118 against a subject's body and moving casing 102 in a distal direction will uncover the distal end of the needle 116. Such relative movement allows the distal end of the needle 116 to extend into the subject's body. Such insertion is termed "manual" insertion as the needle 116 is manually inserted via the subject's manual movement of the casing 102 relative to needle shroud 118. Retraction of the needle shroud 118 into the casing 102 causes the collar 108 to rotate, releasing the plunger 106.

Another form of activation is "automated," whereby the needle 116 moves relative to casing 102. Such insertion can be triggered by movement of the shroud 118 and/or by another form of activation, such as, for example, a button.

Typically, the user presses the needle shroud 118 against an injection site to push the needle shroud 118 at least partially into the device body. The exposed needle 116 is pushed into the injection site. In a holding position, medicament is automatically dispensed from the needle 116 via an automated mechanism. However, a user typically holds the needle shroud 118 in the holding position against the subject's body for a predetermined period of time, to ensure that the correct dose of medicament is dispensed from the device 100, before removing the device from the injection site.

The spring force from the control spring 120 against which the user applies a force to move the needle shroud 118 is one component of an "activation force" of the device 100. The activation force refers to the force or force profile that the user exerts on the device 100 to move the needle shroud 118 from the extended position shown in FIG. 1 to a retracted position. If this force or force profile is not well balanced, it can lead to difficulty in activating the injection device 100 for some users, or increase the pain or anxiety associated with using the injection device 100.

Furthermore, once activated and the needle shroud 118 is in its retracted position, the user continues to apply a "holding force" to counteract the spring force from the control spring 120 to keep the needle 116 pushed into the injection site while minimizing any movement that may cause further pain or discomfort to the subject while medicament from reservoir 104 is delivered. The holding force refers to the force or force profile that the user exerts on the injection device 100 to maintain the needle shroud 118 in the retracted position and keep the needle 116 pushed into the injection site for fully delivering the medicament. If this force or force profile is not well balanced, it can lead to difficulty in administering the correct dosage of medicament to the subject, and increase the likelihood of pain and/or discomfort to the subject, and/or increase the anxiety associated with using the injection device 100.

Following injection, the injection device 100 may be moved proximally from the injection site to remove needle 116 from subject's body in which the needle 116 is automatically retracted within the shroud 118 to substantially a distal position similar to its starting position as depicted in FIG. 1. Retraction can occur when the shroud 118 moves distally under the biasing of the control spring 120 as a user removes the device 100 from a subject's body. Once a distal end of shroud 118 has moved past a distal end of the needle 116, and the needle 116 is covered, the shroud 118 is locked. Such locking can include locking any (substantial) proximal movement of the shroud 118 relative to the casing 102, i.e., to prevent any movement of the shroud 118 that would uncover the needle 116.

FIGS. 2A-D shows an example of the operation of a hold detent mechanism 202 coupled to a needle shroud 204 and injection device body or outer casing 206. The needle shroud 204 and injection device body or outer casing 206 correspond to the needle shroud 118 and outer casing 102 of FIG. 1, but which are further modified to include hold detent mechanism 202.

Figure 2A:
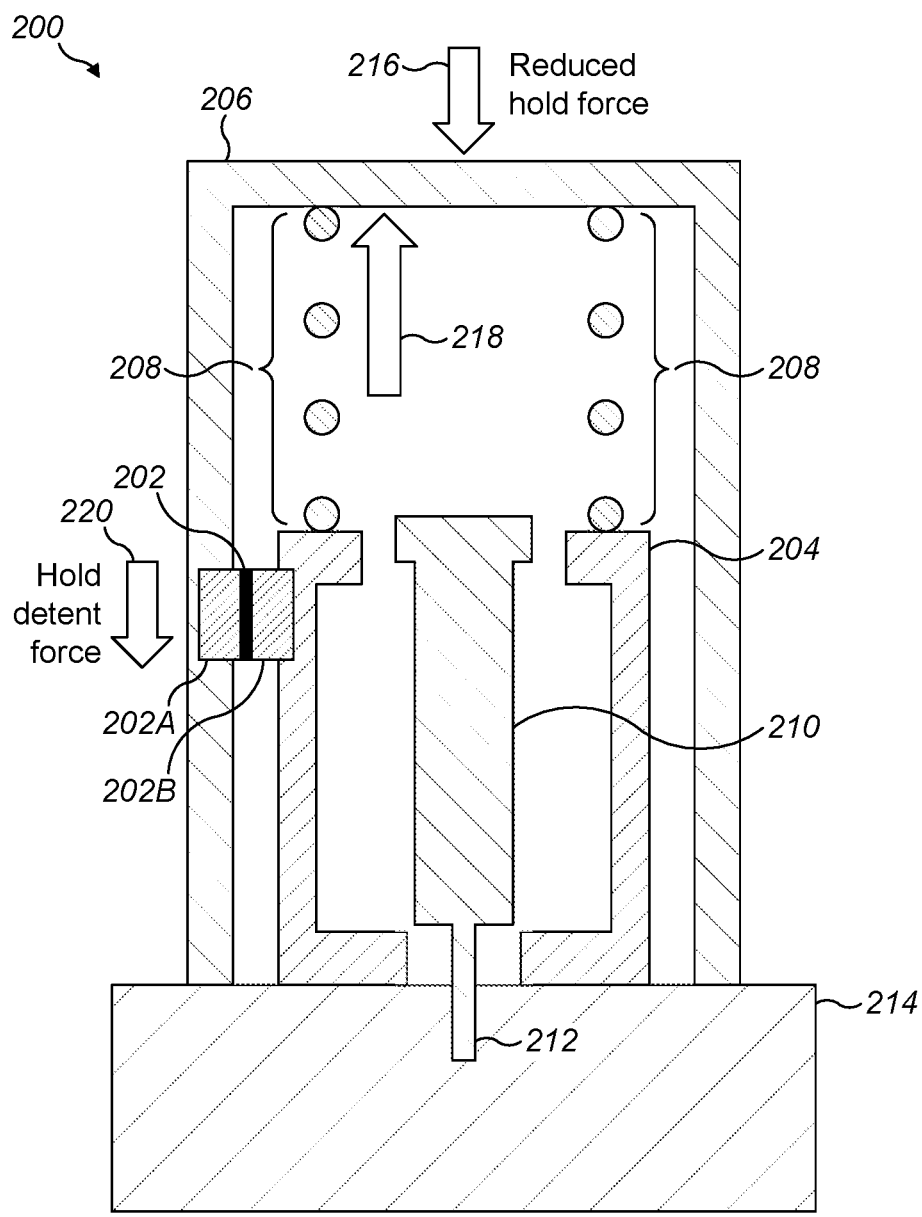
FIG. 2A shows a schematic example of a cross section of an injection device with a hold detent mechanism.

FIG. 2A shows an example of an injection device 200 with a hold detent mechanism 202 and needle shroud 204, e.g., the injection device of FIG. 1. The injection device 200 includes an injection device body or outer casing 206 within which the needle shroud 204 is retractably mounted. The needle shroud 204 is configured to be retractable into the injection device body or outer casing 206. A control spring 208 is coupled to the needle shroud 204 within the injection device body or outer casing 206. The control spring 208 is biased to cause the needle shroud 204 to be at least partially extended from the injection device body or outer casing 206 in an initial position. The injection device 200 further includes a reservoir 210 coupled to a needle 212 at a distal end of the injection device body or outer casing 206.

The hold detent mechanism 202 is coupled to at least the needle shroud 204 and, in this example, to the injection device body or outer casing 206. The hold detent mechanism 203 is configured to activate, when the needle shroud 204 is retracted from an initial position (e.g., as shown in FIG. 1) in which the needle shroud 204 is extended out from the injection device body or outer casing 206 and at least fully covers or encloses the needle 212. Thus, the injection device 200 has a distal end in which the needle shroud 204 extends outside the injection device body or outer casing 206 at an initial position. As depicted in FIG. 2A, a user has already placed the distal end of the injection device 200 (i.e., the distal end of the extended portion of the needle shroud 204) on an injection site of a subject 214 and has also applied an axial hold force 216 to the proximal end of the injection device body or outer casing 206 and along the longitudinal axis of the injection device 200 causing the needle shroud 204 to retract into the injection device body or outer casing 202. The user has applied enough axial hold force 216 to enable the needle shroud 204 to be retracted into the injection device body or outer casing 206 while compressing the control spring 208. During retraction of the needle shroud 204, the needle 212 is exposed and, in this example, enters the subject 214. The control spring 208 exerts a control spring force 218 that is in an opposite direction to the hold force 216 as the user forces the needle shroud 204 to be retracted into the injection device body or outer casing 206 until a hold position is reached. In this example, the hold position is reached when the needle shroud 204 is substantially flush with the distal end of the injection device body or outer casing 206 as depicted in FIG. 2A.

When the hold position is reached, the hold detent mechanism 202 is activated to create a hold detent force 220 in an opposite direction to the control spring force 218 caused by compression of the control spring 208 during said retraction of needle shroud 204 to said hold position. In this example, the hold detent mechanism 202 includes a first hold detent feature 202A coupled to the needle shroud 204, which, when activated, interacts with a second hold detent feature 202B on the injection device body or outer casing 206 for creating the hold detent force 220. In this case, the hold force 216 reduces by an amount substantially equal to the hold detent force 220. This provides the advantage that the user exerts less effort to maintain the needle shroud 204 in the hold position while waiting for the required dosage of medicament from the reservoir 210 to be delivered via needle 212 to the subject 202.

When the medicament is delivered, the user may release the applied reduced hold force 216 in which the first and second hold detent features of the hold detent mechanism 202 deactivate to release the hold detent force 220 and enable the needle shroud 204 to extend from the injection device body or outer casing 206 such that the control spring 208 causes the needle shroud 204 to extend from the injection device body or outer casing 206 as the control spring force overcomes the reduced hold detent force 220 and hold force 216 until the needle shroud 204 substantially reaches the initial position.

Figure 2D:
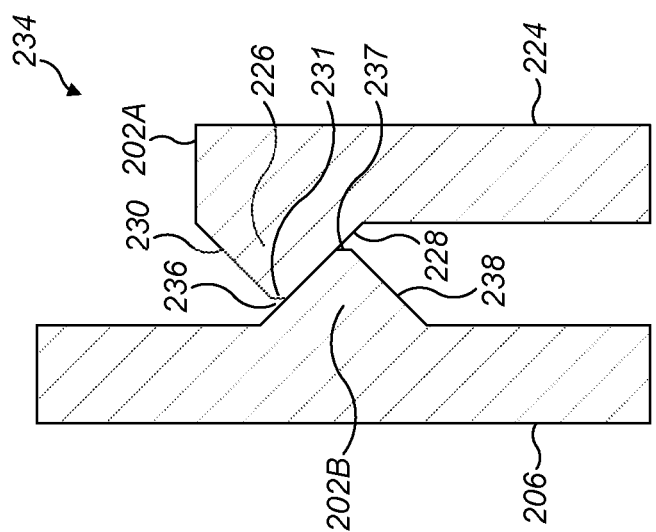
FIG. 2D shows a schematic example of a cross section of a further hold detent mechanism for the injection device of FIG. 2A.
Figure 2C:
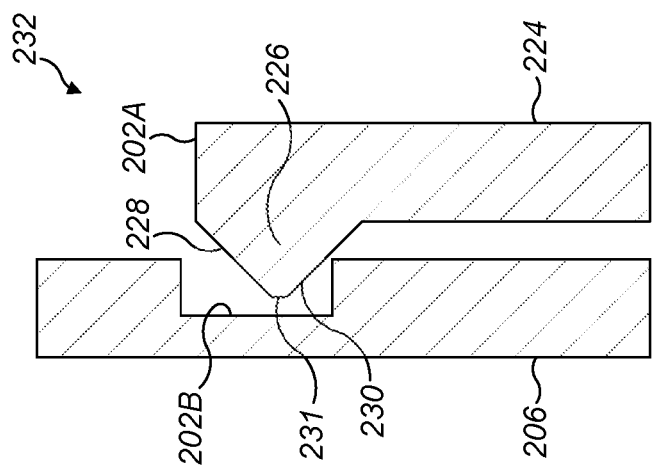
FIG. 2C shows a schematic example of a cross section of another hold detent mechanism for the injection device of FIG. 2A.
Figure 2B:
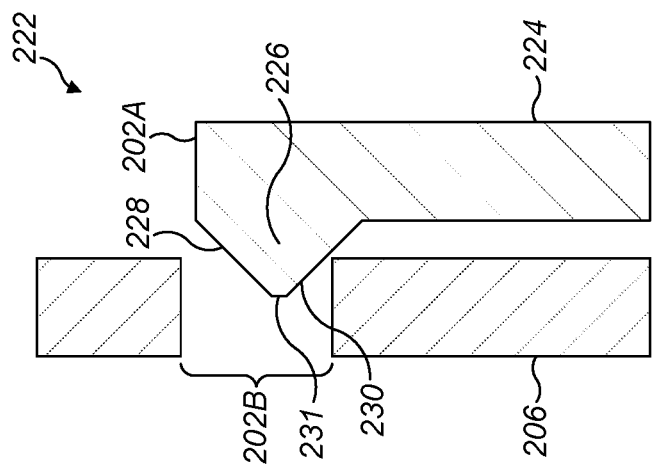
FIG. 2B shows a schematic example of a cross section of a hold detent mechanism for the injection device of FIG. 2A.

FIG. 2B shows an example of a hold detent mechanism 222 includes first and second hold detent features 202A and 202B when activated in the hold position. For simplicity, reference numerals from FIG. 2A are reused for similar or the same components. In this example, the first hold detent feature 202A is coupled to a flexible arm 224 in which the flexible arm 224 forms part of the needle shroud 204 (e.g., a snap fit or integral cut-out). The first hold detent feature 202A includes a male component 226 with a first ramped surface 228 and a second ramped surface 230 extending outwardly from the flexible arm 224. The first and second ramped surfaces 230 and 228 meet at a tip surface 231 of the male component 226 that faces the outer casing 206. The tip surface 231 may be a flat surface or a point. The second hold detent feature 202B is an aperture, hole, or recess through the outer casing 206 that is positioned in the outer casing 206 such that it activates the hold detent mechanism 232 as the needle shroud 204 reaches the hold position. The second hold detent feature 202B is shaped to receive at least a portion of the first and second ramped surfaces 230 and 228 and tip surface 231 of the male component 226 of the first hold detent feature 202A. The second hold detent feature 202B is positioned to enable the hold detent mechanism to activate when the needle shroud 204 approaches and/or reaches the hold position (e.g., the distal end of the needle shroud 204 is substantially flush to the distal end of the outer casing 206).

The tip surface 231 of the male component 224 is configured to be of a size that, for example, reduces friction against the outer casing 206 as the needle shroud 204 retracts into and extracts from the outer casing 206 while still enabling the needle shroud 204 to retract to the holding position and extract back to the final or initial position without substantially affecting the required force the user requires to retract the needle shroud 204. Prior to the needle shroud 204 reaching the hold position, the positioning of the first hold detent feature 202A along with the size of the first and second ramps 228 and 230 of the male component 226 and also the tipped surface 231 are configured to generate a bias force that flexes the flexible arm 224 radially away from the outer casing 206. In this case, due to the biasing of the flexible arm 224, the male component 226 of the flexible arm 224 exerts an opposite force against the outer casing 206.

When the needle shroud 204 approaches the hold position, the second ramp 230 of the male component 226 of the first hold detent feature 202A interacts with the edge of the aperture of the second hold detent feature 202B in which the biassing force causes the edge of the aperture to slide along the ramped surface 230 towards the base of ramped surface 230 of the flexible arm 224 and the flexible arm 224 straightens. For example, when the ramped surface 230 meets the edge of the aperture of the second hold detent feature 202B the biasing force enables the ramped surfaces 228 and 230 and the tip surface 231 of male component 226 to be guided into the aperture. The ramped surface 230 slides along edge of the aperture into the aperture as the bias force applied to the flexible arm 224 reduces causing the flexible arm 224 to flex radially towards the outer casing 206 (i.e., to straighten) until the first and second ramped surfaces 228 and 230 and tipped surface 231 of the male component 226 are substantially within the aperture of the second hold detent feature 202B at the hold position of the needle shroud 204. The hold detent mechanism 232 may said to be activated and exerts a holding force 220 in opposition to the control spring force 218.

The holding force 220 is based, at least in part, on the force required to radially flex the flexible arm 224 away from the outer casing 206 so that the tip surface 231 of the male component 226 can exit the aperture of the second hold detent feature 202B. In this case, when the hold detent mechanism 232 is activated, the hold force 216 reduces by an amount substantially equal to the hold detent force 220, which includes the force required to overcome the biasing force of the flexible arm 226. This provides the advantage that the user exerts less effort to maintain the needle shroud 204 in the hold position while waiting for the required dosage of medicament from the reservoir 210 to be delivered via needle 212 to the subject 202.

When the medicament is delivered, the user may release the applied reduced hold force 216 in which the control spring force 218 of control spring 208 overcomes the hold detent force 220 including the force required to overcome the biasing force of the flexible arm 226 to push the first and second ramped surfaces 228 and 230 and tipped surface 231 of the male component 226 out of the aperture, which flexes the flexible arm 224. Thus, the first and second hold detent features 202A and 202B of the hold detent mechanism 232 deactivate and the hold detent force 220 is released. The control spring 208 causes the needle shroud 204 to extend from the injection device body or outer casing 206 while flexing the flexible arm 224 radially away from the outer casing 206. This causes the needle shroud 204 to extend from the injection device body or outer casing 206 as the control spring force eventually overcomes the hold detent force 220 and hold force 216 until the needle shroud 204 substantially reaches the final and/or initial position.

FIG. 2C shows another example of a hold detent mechanism 232 including first and second hold detent features 202A and 202B when activated in the hold position. For simplicity, reference numerals from FIGS. 2A and 2B are reused for similar or the same components. In this example, the first hold detent feature 202A is the same as the first hold detent feature 202A of FIG. 2B. In this example, the second hold detent feature 202B is a partial recess into the inner surface of the outer casing, or an indented surface within the outer casing, and is shaped to receive at least a portion of the first and second ramped surfaces 230 and 228 and tip surface 231 of the male component 226 of the first hold detent feature 202A. The second hold detent feature 202B is positioned on the outer casing 206 to enable the hold detent mechanism 232 to activate when the needle shroud 204 approaches and/or reaches the hold position (e.g., the distal end of the needle shroud 204 is substantially flush to the distal end of the outer casing 206). The hold detent mechanism 232 activates and deactivates in a similar manner as the hold detent mechanism 222 as described with reference to FIG. 2B.

FIG. 2D shows a further example of a hold detent mechanism 234 including first and second hold detent features 202A and 202B when activated in the hold position. For simplicity, reference numerals from FIGS. 2A to 2C are reused for similar or the same components. In this example, the first hold detent feature 202A is coupled to a flexible arm 224 in which the flexible arm 224 forms part of the needle shroud 204 (e.g., a snap fit or integral cut-out). The first hold detent feature 202A includes a male component 226 with a first ramped surface 228 and a second ramped surface 230 extending outwardly from the flexible arm 224. The first and second ramped surfaces 230 and 228 meet at a tip surface 231 of the male component 226 that faces the outer casing 206. The tip surface 231 may be a flat surface or a point. In this example, the flexible arm 224 of the first hold detent feature 202A is not flexed by a biassing force as described in FIG. 2B or 2C. The second hold detent feature 202B has a corresponding male component including a first ramp surface 236 and second ramp surface 238 with gradients directed radially inwards or towards the longitudinal axis of the injection device 200 that meet at a tip surface 237 or at a point. The second hold detent feature 202B is positioned on the inner surface of the outer casing 206 it activates the hold detent mechanism 232 as the needle shroud 204 reaches the hold position. The second hold detent feature 202B is positioned to enable the hold detent mechanism 234 to activate when the needle shroud 204 approaches and/or reaches the hold position (e.g., the distal end of the needle shroud 204 is substantially flush to the distal end of the outer casing 206).

Prior to the needle shroud 204 reaching the hold position, the flexible arm 224 of the first hold detent feature 202A is not biased against the outer casing 206. When the needle shroud 204 approaches the hold position, the first ramp surface 230 of the male component 226 of the first hold detent feature 202A interacts with second ramp surface 238 of the male component of the second hold detent feature 202B to bias the flexible arm 224 radially away from the outer casing 206. In this manner, the male component 226 of the first hold detent feature 202A travels over the second ramped surface 238. The second ramped surface 238 of the second hold detent feature 202B is shaped to guide the first ramped surface 230 to bias the flexible arm 224 radially away from the outer casing 206. As the needle shroud 204 approaches the hold position, the second ramped surface 238 guides the male component 226 over the tip surface 237 of the male component of the second hold detent feature 202B the biassing force applied to the flexible arm 224 is maximized.

Once the tip surface 231 of the male component 226 of the first hold detent feature 202A travels over the tip surface 237 of the male component of the second hold detent feature 202B, the biassing force applied to the flexible arm 224 as the male component 226 of the first hold detent feature 202A is deflected over the male component of the second hold detent feature 202B and causes the second ramped surface 228 to engage with the first ramped surface 236 of the male component of the second hold detent feature 202B. The first ramped surface 236 of the male component of the second hold detent feature 202B guides the flexible arm 224 towards the hold position. The second ramped surface 228 of the first hold detent feature 202A slides along the first ramped surface 236 of the second hold detent feature 202B as the bias force applied to the flexible arm 224 reduces causing the flexible arm 224 to flex radially towards the outer casing 206 (i.e., to straighten) until needle shroud 204 reaches the hold position. The hold detent mechanism 234 may be said to be activated in which the biasing force required to move the male component 226 of the first hold detent feature 202A back over the male component of the second hold detent feature 202B in the distal direction forms a holding force 220 in opposition to the control spring force 218. The holding force 220 is based, at least in part, on the force required to radially flex the flexible arm 224 away from the outer casing 206 so that the tip surface 231 of the male component 226 can move over the tip surface 237 of the male component of the second hold detent feature 202B. In this case, when the hold detent mechanism 232 is activated, the hold force 216 reduces by an amount substantially equal to the hold detent force 220, which includes the force required to overcome the biasing force of the flexible arm 226. This provides the advantage that the user exerts less effort to maintain the needle shroud 204 in the hold position while waiting for the required dosage of medicament from the reservoir 210 to be delivered via needle 212 to the subject 202.

When the medicament is delivered, the user may release the applied reduced hold force 216 in which the control spring force 218 of control spring 208 overcomes the hold detent force 220 including the force required to bias the flexible arm 226 radially away from the outer casing 206 to push the second ramped surface 228 and tipped surface 237 of the male component 226 along the first ramped surface 236 and over the tipped surface 237 of the male component of the second hold detent feature 202B, which flexes the flexible arm 224. Once this is achieved, the first and second hold detent features 202A and 202B of the hold detent mechanism 232 deactivates and the hold detent force 220 is released. The control spring 208 continues to cause the needle shroud 204 to extend from the injection device body or outer casing 206 as the biassing force is removed from the flexible arm 224, which unflexes radially towards the outer casing 206 to a relaxed state (e.g., straightened). This causes the needle shroud 204 to extend from the injection device body or outer casing 206 once the control spring force overcomes the hold detent force 220 and hold force 216 until the needle shroud 204 substantially reaches the final and/or initial position.

FIGS. 2E-2H shows another example of the operation of another hold detent mechanism 242 coupled to a needle shroud 204 and a collar 244. For simplicity, reference numerals from FIGS. 2A to 2D are reused for similar or the same components. The needle shroud 204 and collar 244 also substantially correspond to the needle shroud 118 and collar 108 of FIG. 1, but which are further modified to include hold detent mechanism 242.

Figure 2E:
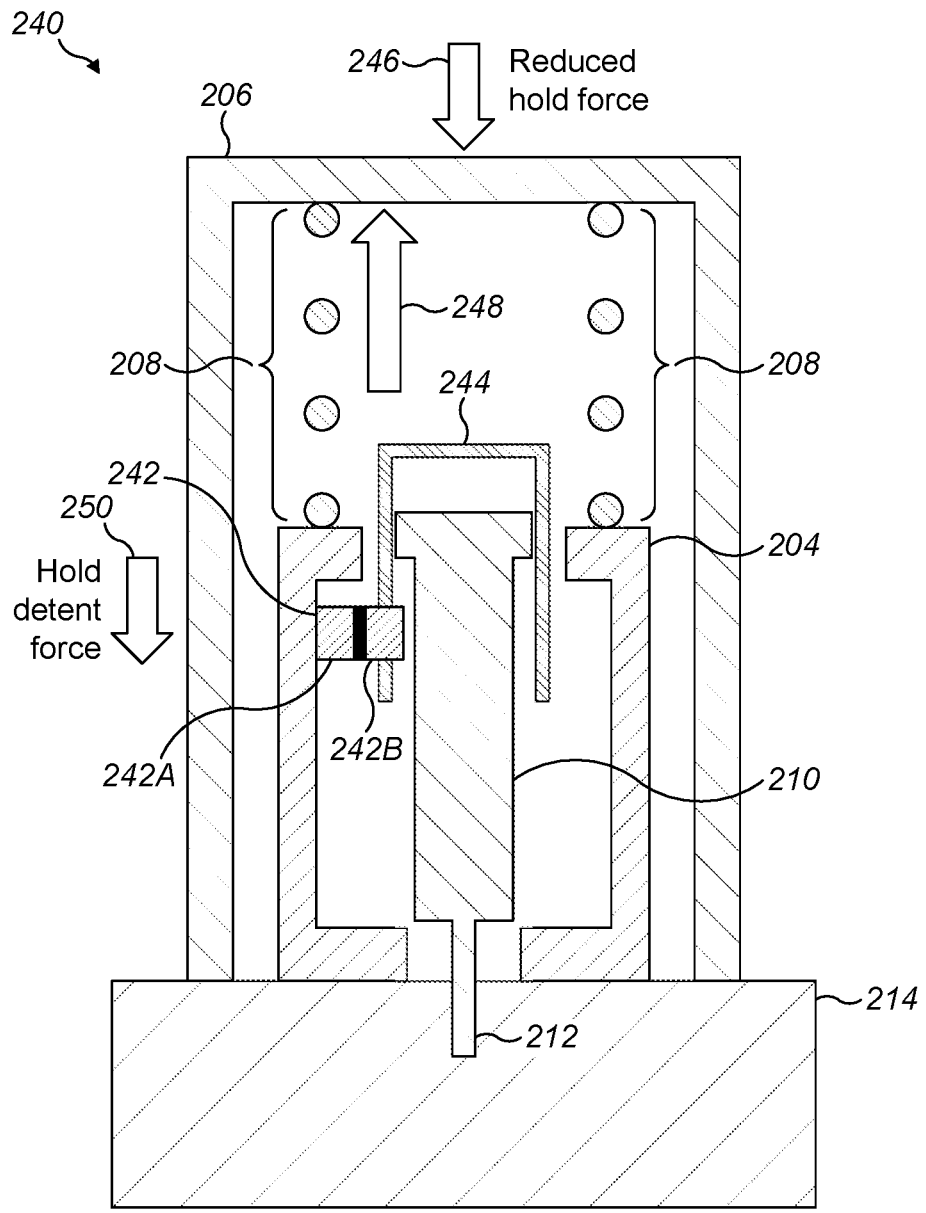
FIG. 2E shows a schematic example of a cross section of another injection device with a hold detent mechanism.

FIG. 2E shows another example of an injection device 240 with a hold detent mechanism 242 and needle shroud 204, e.g., similar to the injection device of FIG. 1. For simplicity, reference numerals from FIGS. 2A to 2D are reused for similar or the same components. The injection device 240 includes an injection device body or outer casing 206 within which the needle shroud 204 is retractably mounted. The needle shroud 204 is configured to be retractable into the injection device body or outer casing 206. A control spring 208 is coupled to the needle shroud 204 within the injection device body or outer casing 206. The control spring 208 is biased to cause the needle shroud 204 to be at least partially extended from the injection device body or outer casing 206 in the initial position. The injection device 200 further includes a reservoir 210 coupled to a needle 212 at a distal end of the injection device body or outer casing 206.

In this example, a collar 244 of the injection device 240 is also illustrated in which the collar 244 is configured to guide the needle shroud 204 during retraction and extraction with respect to the injection device body or outer casing 206. In some embodiments, during retraction of the needle shroud 204, the collar 244 is configured to rotate in which a pin on the needle shroud 204 mates with a track on the collar 244 for guiding, as the collar 244 rotates, the needle shroud 204 to a hold position. In some embodiments, during extraction of the needle shroud 204, the pin of the needle shroud 204 is guided along a further track in the collar 244 for guiding, as the collar rotates 244, the needle shroud 204 to extract from the injection device body or outer casing 206 to a final position, which may be substantially similar to the initial position, in which at least a portion of the needle shroud 204 is extracted outside the injection device body or outer casing 206 and substantially or fully covers or encloses the needle 212 for disposal.

The hold detent mechanism 242 is coupled to at least the needle shroud 204 and, in this example, to the collar 244. The hold detent mechanism 242 is configured to activate, when the needle shroud 204 is retracted from an initial position (e.g., as shown in FIG. 1) in which the needle shroud 204 is extended out from the injection device body or outer casing 206 and at least fully covers or encloses the needle 212. Thus, the injection device 240 has a distal end in which the needle shroud 204 extends outside the injection device body or outer casing 206 at an initial position. As depicted in FIG. 2E, a user has already placed the distal end of the injection device 240 (i.e., the distal end of the extended portion of the needle shroud 204) on an injection site of a subject 214 and has also applied an axial hold force 246 to the proximal end of the injection device body or outer casing 206 and along the longitudinal axis of the injection device 240 causing the needle shroud 204 to retract into the injection device body or outer casing 202. The user has applied enough axial hold force 246 to enable the needle shroud 204 to be retracted into the injection device body or outer casing 206 while compressing the control spring 208. During retraction of the needle shroud 204, the needle 212 is exposed and, in this example, enters the subject 214. The control spring 208 exerts a control spring force 248 that is in an opposite direction to the hold force 246 as the user forces the needle shroud 204 to be retracted into the injection device body or outer casing 206 until a hold position is reached. In this example, the hold position is reached when the needle shroud 204 is substantially flush with the distal end of the injection device body or outer casing 206 as depicted in FIG. 2E.

When the hold position is reached, the hold detent mechanism 242 is activated to create a hold detent force 240 in an opposite direction to the control spring force 248 caused by compression of the control spring 208 during said retraction of needle shroud 204 to said hold position. In this example, the hold detent mechanism 242 includes a first hold detent feature 242a coupled to the needle shroud 204 and a second hold detent feature 242b coupled to the collar 244, which, when activated, interacts with a second hold detent feature 242b on the collar 244 for creating the hold detent force 250. In this case, the hold force 246 reduces by an amount substantially equal to the hold detent force 250. This provides the advantage that the user exerts less effort to maintain the needle shroud 204 in the hold position while waiting for the required dosage of medicament from the reservoir 210 to be delivered via needle 212 to the subject 214.

When the medicament is delivered, the user may release the applied reduced hold force 246 in which the first and second hold detent features 242a and 242b of the hold detent mechanism 242 deactivate to release the hold detent force 250 in which the control spring force 248 causes and/or enables the needle shroud 204 to extend from the injection device body or outer casing 206 such that the control spring 208 causes the needle shroud 204 to extend from the injection device body or outer casing 206 as the control spring force overcomes the reduced hold detent force 250 and hold force 246 until the needle shroud 204 substantially reaches a final position substantially similar or the same as the initial position.

FIG. 2F shows an example of a hold detent mechanism 252 including first and second hold detent features 242A and 242B when activated in the hold position. For simplicity, reference numerals from FIG. 2E are reused for similar or the same components. In this example, the first hold detent feature 242A is coupled to a flexible arm 224 in which the flexible arm 224 forms part of the needle shroud 204 (e.g., a snap fit or integral cut-out). The first hold detent feature 242A includes a male component 226 with a first ramped surface 228 and a second ramped surface 230 extending inwardly from the flexible arm 224 towards the longitudinal axis of the injection device 240. The first and second ramped surfaces 230 and 228 meet at a tip surface 231 of the male component 226 that faces towards the outer surface of the collar 244. The tip surface 231 may be a flat surface or a point. The second hold detent feature 242B is an aperture, hole, or recess through the collar 244 that is positioned in the collar 244 such that it activates the hold detent mechanism 252 as the needle shroud 204 reaches the hold position. The second hold detent feature 242B is shaped to receive at least a portion of the first and second ramped surfaces 230 and 228 and tip surface 231 of the male component 226 of the first hold detent feature 242A. The second hold detent feature 242B is positioned on the collar 244 to enable the hold detent mechanism 252 to activate when the needle shroud 204 approaches and/or reaches the hold position (e.g., the distal end of the needle shroud 204 is substantially flush to the distal end of the outer casing 206).

The tip surface 231 of the male component 226 is configured to be of a size that, for example, reduces friction against the outer surface of the collar 244 as the needle shroud 204 retracts into and extracts from the outer casing 206 while still enabling the needle shroud 204 to retract to the holding position and extract back to the final or initial position without substantially affecting the required force the user requires to retract the needle shroud 204. Prior to the needle shroud 204 reaching the hold position, the positioning of the first hold detent feature 242A along with the size of the first and second ramps 228 and 230 of the male component 226 and also the tipped surface 231 are configured to generate a bias force that flexes the flexible arm 224 radially away from the outer surface of the collar 244. In this case, due to the biasing of the flexible arm 224, the male component 226 of the flexible arm 224 exerts an opposite force against the collar 244 206 in the direction towards the outer casing 206.

When the needle shroud 204 approaches the hold position, the second ramp 230 of the male component 226 of the first hold detent feature 242A interacts or engages with the edge of the aperture of the second hold detent feature 242B in which the biassing force causes the edge of the aperture to slide along the ramped surface 230 towards the base of ramped surface 230 of the flexible arm 224 and the flexible arm 224 unflexes and/or straightens. For example, when the ramped surface 230 meets the edge of the aperture of the second hold detent feature 242B the biasing force enables the ramped surfaces 228 and 230 and the tip surface 231 of male component 226 to be guided into the aperture. The ramped surface 230 slides along edge of the aperture into the aperture as the bias force applied to the flexible arm 224 reduces causing the flexible arm 224 to flex radially towards the collar 244 (i.e., to straighten) until the first and second ramped surfaces 228 and 230 and tipped surface 231 of the male component 226 are substantially within the aperture of the second hold detent feature 242B at the hold position of the needle shroud 204. The hold detent mechanism 252 may said to be activated and exerts a holding force 250 in opposition to the control spring force 248.

The holding force 250 is based, at least in part, on the force required to radially flex the flexible arm 224 away from the outer surface of the collar 244 so that the tip surface 231 of the male component 226 can exit the aperture of the second hold detent feature 242B. In this case, when the hold detent mechanism 252 is activated, the hold force 246 reduces by an amount substantially equal to the hold detent force 250, which includes the force required to overcome the biasing force of the flexible arm 224. This provides the advantage that the user exerts less effort to maintain the needle shroud 204 in the hold position while waiting for the required dosage of medicament from the reservoir 210 to be delivered via needle 212 to the subject 214.

When the medicament is delivered, the user may release the applied reduced hold force 246 in which the control spring force 248 of control spring 208 overcomes the hold detent force 250 including the force required to overcome the biasing force of the flexible arm 224 to push the first and second ramped surfaces 228 and 230 and tipped surface 231 of the male component 226 out of the aperture, which flexes the flexible arm 224. Thus, the first and second hold detent features 242A and 242B of the hold detent mechanism 252 deactivates and the hold detent force 250 is released. The control spring 208 causes the needle shroud 204 to extend from the injection device body or outer casing 206 while flexing the flexible arm 224 radially away from the collar 244. This causes the needle shroud 204 to extend from the injection device body or outer casing 206 as the control spring force eventually overcomes the hold detent force 250 and hold force 246 until the needle shroud 204 substantially reaches the final and/or initial position.

FIG. 2G shows another example of a hold detent mechanism 254 including first and second hold detent features 242A and 242B when activated in the hold position. For simplicity, reference numerals from FIGS. 2E and 2F are reused for similar or the same components. In this example, the first hold detent feature 242A is the same as the first hold detent feature 242A of FIG. 2F. In this example, the second hold detent feature 242B is a partial recess into the outer surface of the collar 244, or an indented surface within the outer surface of the collar 244, and is shaped to receive at least a portion of the first and second ramped surfaces 230 and 228 and tip surface 231 of the male component 226 of the first hold detent feature 242A. The second hold detent feature 242B is positioned on the collar 244 to enable the hold detent mechanism 254 to activate when the needle shroud 204 approaches and/or reaches the hold position (e.g., the distal end of the needle shroud 204 is substantially flush to the distal end of the outer casing 206). The hold detent mechanism 254 activates and deactivates in a similar manner as the hold detent mechanism 252 as described with reference to FIG. 2F.

FIG. 2H shows a further example of a hold detent mechanism 256 including first and second hold detent features 242A and 242B when activated in the hold position. For simplicity, reference numerals from FIGS. 2E to 2G are reused for similar or the same components. In this example, the first hold detent feature 242A is coupled to a flexible arm 224 in which the flexible arm 224 forms part of the needle shroud 204 (e.g., a snap fit or integral cut-out). The first hold detent feature 242A includes a male component 226 with a first ramped surface 228 and a second ramped surface 230 extending outwardly from the flexible arm 224 in the direction of the collar 244. The first and second ramped surfaces 230 and 228 meet at a tip surface 231 of the male component 226 that faces the outer surface of the collar 244. The tip surface 231 may be a flat surface or a point. In this example, the flexible arm 224 of the first hold detent feature 242A is not flexed by a biasing force as described in FIG. 2F or 2G. The second hold detent feature 242B has a corresponding male component including a first ramp surface 236 and second ramp surface 238 with gradients directed radially outwardly, towards the flexible arm 224 or away from the longitudinal axis of the injection device 200 that meet at a tip surface 237 or at a point. The second hold detent feature 242B is positioned on the outer surface of the collar 244 it activates the hold detent mechanism 256 as the needle shroud 204 reaches the hold position. The second hold detent feature 242B is positioned to enable the hold detent mechanism 256 to activate when the needle shroud 204 approaches and/or reaches the hold position (e.g., the distal end of the needle shroud 204 is substantially flush to the distal end of the outer casing 206).

Prior to the needle shroud 204 reaching the hold position, the flexible arm 224 of the first hold detent feature 242A is not biased against the outer surface of the collar 244. When the needle shroud 204 approaches the hold position, the first ramp surface 230 of the male component 226 of the first hold detent feature 242A interacts with second ramp surface 238 of the male component of the second hold detent feature 242B to bias the flexible arm 224 radially away from the outer surface of collar 244. In this manner, the male component 226 of the first hold detent feature 242A travels over the second ramped surface 238. The second ramped surface 238 of the second hold detent feature 242B is shaped to guide the first ramped surface 230 to bias the flexible arm 224 radially away from the outer surface of the collar 244. As the needle shroud 204 approaches the hold position, the second ramped surface 238 guides the male component 226 over the tip surface 237 of the male component of the second hold detent feature 242B the biasing force applied to the flexible arm 224 is maximized.

Once the tip surface 231 of the male component 226 of the first hold detent feature 242A travels over the tip surface 237 of the male component of the second hold detent feature 242B, the biasing force applied to the flexible arm 224 as the male component 226 of the first hold detent feature 242A is deflected over the male component of the second hold detent feature 242B causes the second ramped surface 228 to engage with the first ramped surface 236 of the male component of the second hold detent feature 242B. The first ramped surface 236 of the male component of the second hold detent feature 242B guides the flexible arm 224 towards the hold position. The second ramped surface 228 of the first hold detent feature 242A slides along the first ramped surface 236 of the second hold detent feature 242B as the bias force applied to the flexible arm 224 reduces causing the flexible arm 224 to flex radially towards the outer surface of the collar 244 (i.e., to straighten) until needle shroud 204 reaches the hold position. The hold detent mechanism 256 may be said to be activated in which the biasing force required to move the male component 226 of the first hold detent feature 242A back over the male component of the second hold detent feature 242B in the distal direction forms a holding force 250 in opposition to the control spring force 248. The holding force 250 is based, at least in part, on the force required to radially flex the flexible arm 224 away from the outer surface of the collar 244 so that the tip surface 231 of the male component 226 can move over the tip surface 237 of the male component of the second hold detent feature 242B. In this case, when the hold detent mechanism 256 is activated, the hold force 246 reduces by an amount substantially equal to the hold detent force 250, which includes the force required to overcome the biasing force of the flexible arm 224. This provides the advantage that the user exerts less effort to maintain the needle shroud 204 in the hold position while waiting for the required dosage of medicament from the reservoir 210 to be delivered via needle 212 to the subject 202.

When the medicament is delivered, the user may release the applied reduced hold force 246 in which the control spring force 248 of control spring 208 overcomes the hold detent force 250 including the force required to bias the flexible arm 226 radially away from the outer surface of the collar 244 to push the second ramped surface 228 and tipped surface 237 of the male component 226 along the first ramped surface 236 and over the tipped surface 237 of the male component of the second hold detent feature 242B, which flexes the flexible arm 224. Once this is achieved, the first and second hold detent features 242A and 242B of the hold detent mechanism 256 deactivate and the hold detent force 250 is released. The control spring 208 continues to cause the needle shroud 204 to extend from the injection device body or outer casing 206 as the biassing force is removed from the flexible arm 224, which unflexes radially towards the outer surface of the collar 244 to a relaxed state (e.g., straightened). This causes the needle shroud 204 to extend from the injection device body or outer casing 206 once the control spring force overcomes the hold detent force 250 and hold force 246 until the needle shroud 204 substantially reaches the final and/or initial position.

FIGS. 3A-3F shows an example of the operation of an injection device 300 with a hold detent mechanism formed from a pair of first hold detent features 302A-1/302A-2 and a pair of second hold detent features 302B-1/203B-2. The hold detent mechanism and needle shroud 304-1/304-2 corresponds to the hold detent mechanism 202 and needle shroud 204 of FIGS. 2A and 2B.

Figure 3A:
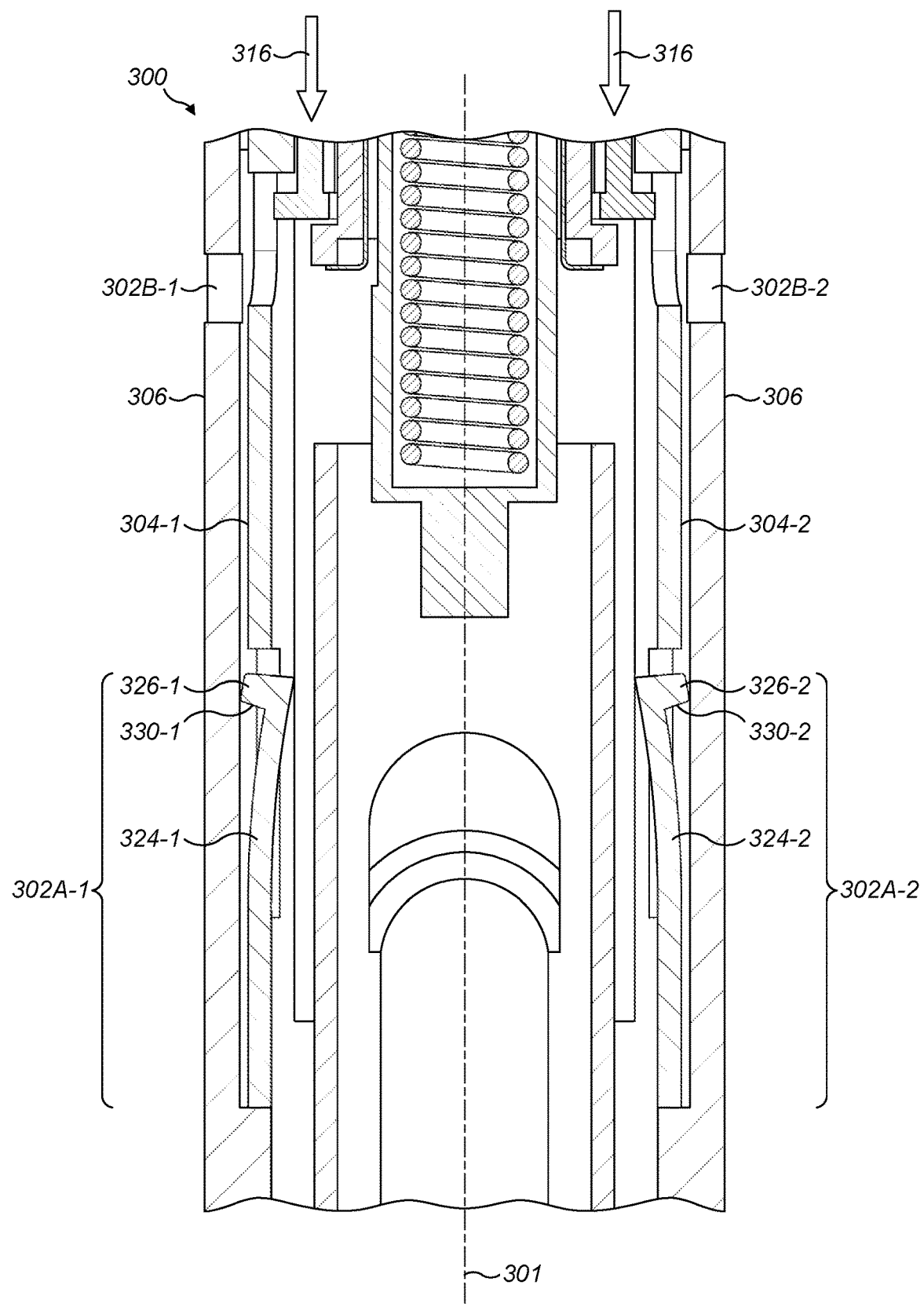
FIG. 3A-3F shows a schematic example of the operation of a cross section portion of an injection device with a hold detent mechanism.

FIG. 3A shows an example of an initial configuration of the hold detent mechanism and needle shroud 304 prior to retraction of the needle shroud 304 of injection device 300 into the injection device body 306, e.g., a pre-activation phase from the initial position. The needle shroud 304 is in an extended position and covers a needle of the injection device. The needle shroud 304 is held in the initial position under a control spring force from a control spring. The first hold detent features 302A-1 and 302A-2 are flexible clips or arms 324-1 and 324-2, respectively, that couple (e.g. snap fit, or a cut-out detent feature) to the outer surface or outside face of the needle shroud 304 with outward facing male components 326-1 and 326-2, respectively, that are configured to engage with the second hold detent features 302B-1 and 302B-2, respectively, when needle shroud 304 is in the hold position (e.g., full needle shroud 304 depression). The second hold detent features 302B-1 and 302B-2 are mating slots or holes through the outer casing 306 of the injection device 300 and are shaped or configured to engage with and receive the respective male components 326-1 and 326-2 of the first hold detent features 302A-1 and 302A-2, respectively. When the male components 326-1 and 326-of the first hold detent features 302A-1 and 302A-2, respectively, are activated or engaged with the corresponding slots of the second hold detent features 302B-1 and 302B-2, the first hold detent features 302A-1 and 302A-2 partially support the control spring force for the duration of the user's 'Hold' when the needle shroud 304 of the injection device 300 is in the hold position.

FIG. 3A illustrates the state of the hold detent mechanism and needle shroud 304 of injection device 300 in a pre-activation phase of the hold detent mechanism in which the male components 326-1 and 326-2 on the flexible arms 324-1 and 324-2 of the first hold detent features 302A-1 and 302A-2, respectively, (e.g., resilient arms or clips) are biased against the outer casing 306 of the injection device 300, which biases and causes the flexible arms 324-1 and 324-2 to flex radially inwards towards the longitudinal axis 301 of the injection device 300. With the flexible arms 324-1 and 324-2 being radially flexed inwards, the male components 326-1 and 326-1 of the flexible arms 324-1 and 324-2, respectively, apply a corresponding small force radially to the inner surface of the injection device body or outer casing 306. This will be reflected in a small and consistent increase in the required injection device activation force 316 that the user applies due to the additional source of friction of the flexible arms 324-1 and 324-2 of the first hold detent features 302A-1 and 302A-2, respectively, as they travel towards the second hold detent features 302B-1 and 302B-2 during the injection device 300 activation phase. In this case, the hold detent mechanism has not been activated as the first hold detent features 302A-1 and 302A-2 have not yet engaged with the second hold detent features 302B-1 and 302B-2, respectively.

In the injection device 300 activation phase, the user applies an activation force 316 that presses the needle shroud 304 against the flesh around an injection site of a subject and the user presses on the proximal end of the injection device 300 to apply activation force 316 as described with reference to FIGS. 2A to 2F. Once this user activation force 316 overcomes the control spring force of the control spring of the injection device 300 it causes the needle shroud 304 to retract into the injection device body or outer casing 304. As the needle shroud 304 retracts, this enables a needle to penetrate the injection site of the subject for delivering a dosage of a medicament during the hold position of the injection device 300. The needle shroud 304 reaches the hold position when the distal end of the needle shroud is substantially flush with the outer casing 302 of the injection device 300. At this point, the activation force 316 turns into a user hold force 317 which the user continues to apply to hold the needle shroud in the retracted hold position. The user hold force 317 may be less than or equal to the user activation force 316. The corresponding first hold detent features 302A-1 and 302A-2 of the needle shroud 304 move with the needle shroud 304 (as the needle shroud 304 retracts) in a direction parallel to the longitudinal axis 301 towards the second hold detent features 302B-1 and 302B-2. In this example, the corresponding slots of the second hold detent features 302B-1 and 302B-2 are positioned on the outer casing 306 such that, when the needle shroud 304 reaches the hold position, the hold detent mechanism activates in which first hold detent features 302A-1 and 302A-2 will engage or latch with the second hold detent features 302B-1 and 302B-2, respectively, as shown in FIGS. 3B and 3C.

Figure 3B:
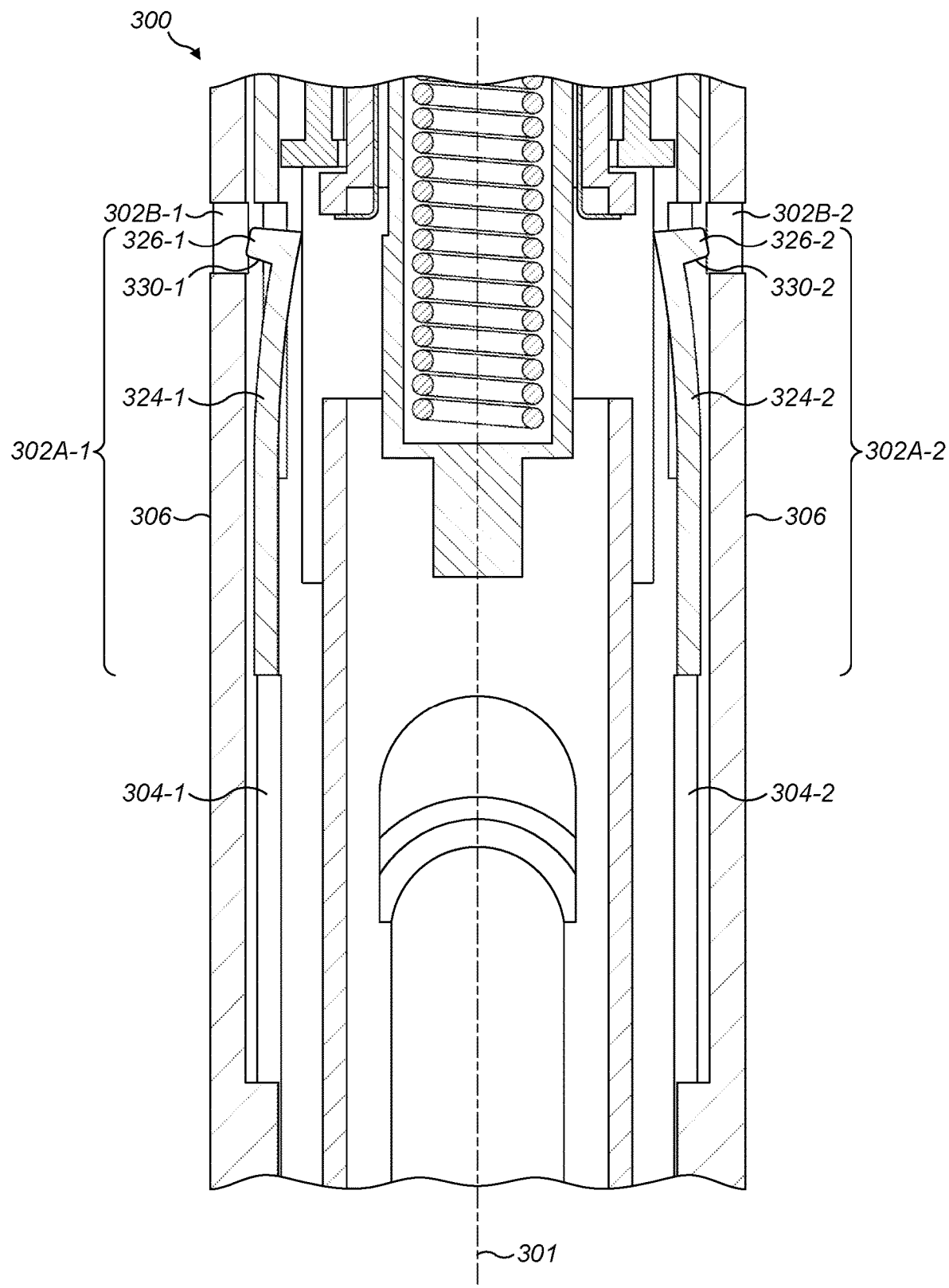

FIG. 3B shows an example of the end of the activation phase of the injection device 300 in which the needle shroud 304 has retracted to the hold position, where the user presses the needle shroud 304 against the flesh around the injection site of a subject. The activation force 316 changes to a user holding force 317 in which the user is required to continue to apply a force in the form of a holding force to the proximal end of the injection device 300 (e.g., to the rear casing 114 of the injection device 100 of FIG. 1) for a period of time during which a dosage of medicament is delivered via needle of the injection device 300 to the subject. The user holding force 317 may be less than or equal to the activation force 316. As illustrated in FIG. 3B, the hold detent mechanism is activated by the male components 326-1 and 326-2 of the first hold detent features 302A-1 and 302A-2 starting to engage with the slots of the second hold detent features 302B-1 and 302B-2, respectively. As the male components 326-1 and 326-2 start to engage the slots, the biassing force against the outer casing 306 that flexes the corresponding flexible arms 324-1 and 324-2 during the activation phase of the injection device 300 starts to release as the male components 326-1 and 326-2 start to engage with slots of the second hold detent features 302B-1 and 302B-2, respectively. As will be seen in the example of FIG. 3C, this engagement causes the flexible arms 324-1 and 324-2 to return to their original configuration (e.g., straighten) and flex radially outwards towards the inner surface of the outer casing 306, while the male components 326-1 and 326-2 enter the slots of the second hold detent features 302B-1 and 302B-2, respectively. The hold detent mechanism is said to be activated when the male components 326-1 and 326-2 start to and fully engage with the slots of the second hold detent features 302B-1 and 302B-2.

Figure 3C:
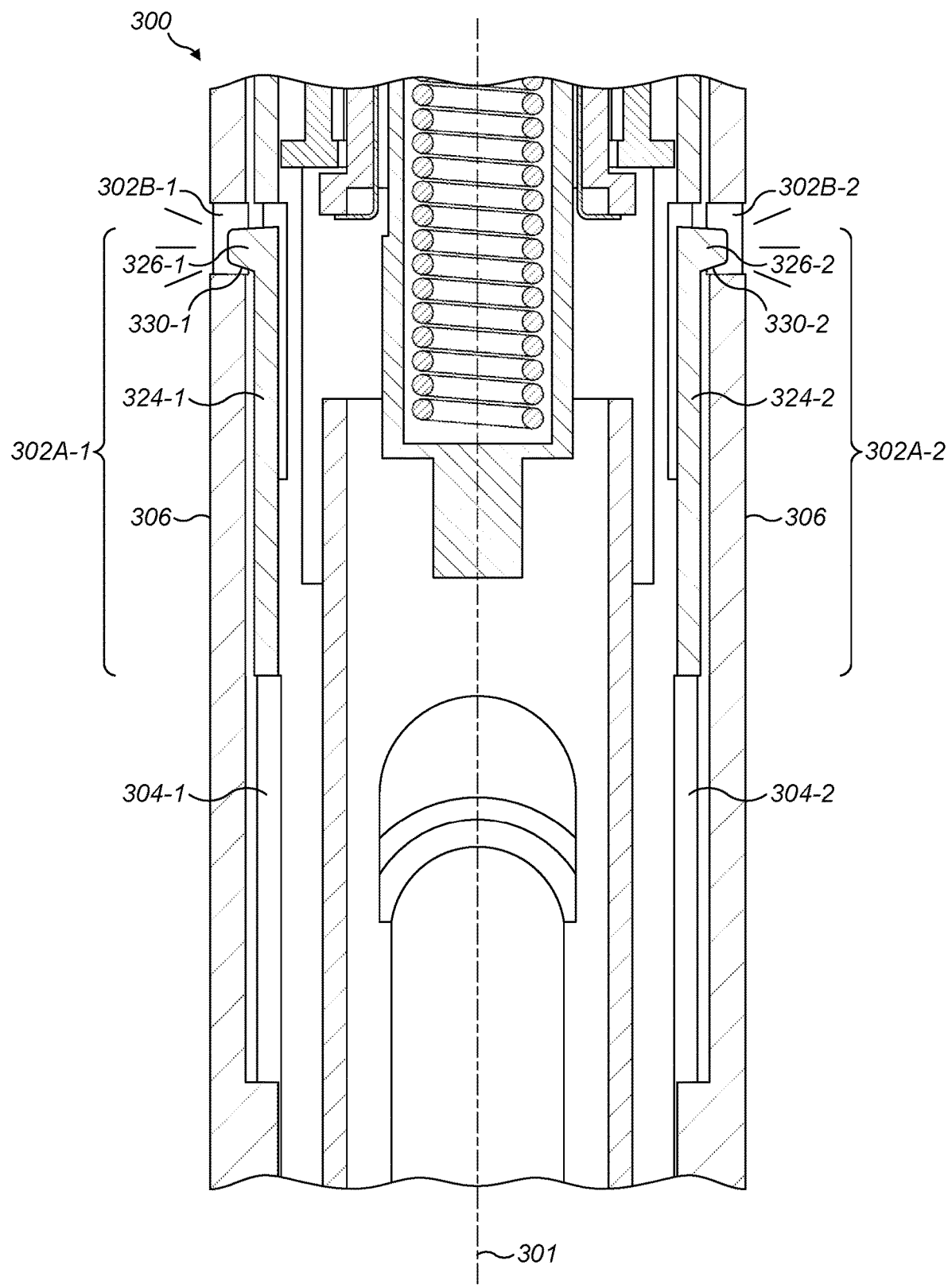

FIG. 3C shows an example of a hold configuration of the hold detent mechanism when activated with the needle shroud 304 in the hold position, e.g., the configuration where the user applies a holding force to the proximal end of the injection device 300 to maintain the hold position while a dosage of medicament is being expelled from the injection device 300 via the needle. In the hold position, the male components 326-1 and 326-2 of the first hold detent features 302A-1 and 302A-2, respectively, have fully engaged the slots of the second hold detent features 302B-1 and 302B-2, respectively. The male components 326-1 and 326-2 engage and latch with the slots. When latched, the ramped surfaces 330-1 and 330-2 of the male components 326-1 and 326-2 engage with the edge of the slots to provide hold detent force that supports a portion of the user holding force against the control spring force of the control spring. In this case, when the hold detent mechanism is activated, the user holding force reduces by an amount substantially equal to the hold detent force, which includes the force required to bias the flexible arms 324-1 and 324-2 radially inwardly towards the longitudinal axis 301 of the injection device 300.

This provides the advantage that the user exerts less effort to maintain the needle shroud 304 in the hold position while waiting for the required dosage of medicament from a reservoir of the injection device 300 to be delivered via needle of the injection device 300 to the subject.

Figure 3D:
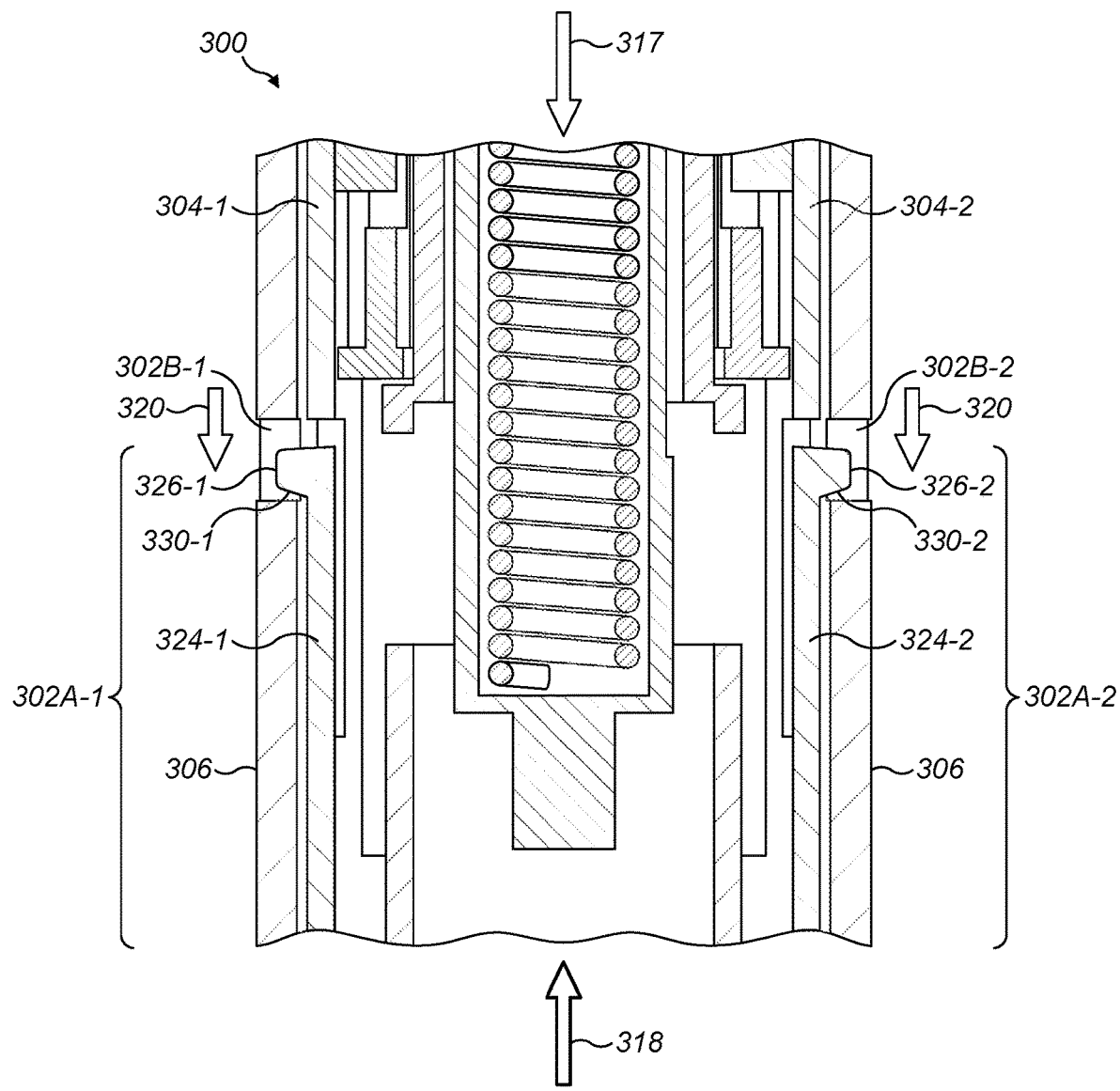

FIG. 3D shows an example of the activation of the hold detent mechanism when the male components 326-1 and 326-2 have latched with corresponding slots of the outer casing 306 to provide corresponding hold detent forces 320 that support the user holding force 317 in opposition to the control spring force 318. The user holding force 317 reduces by an amount substantially equal to the hold detent forces 320, which includes the force required to bias the flexible arms 324-1 and 324-2 radially inwardly towards the longitudinal axis 301 of the injection device 300. Thus, the user exerts less effort to maintain the needle shroud 304 in the hold position while waiting for the required dosage of medicament from a reservoir of the injection device 300 to be delivered via needle of the injection device 300 to the subject.

Figure 3E:
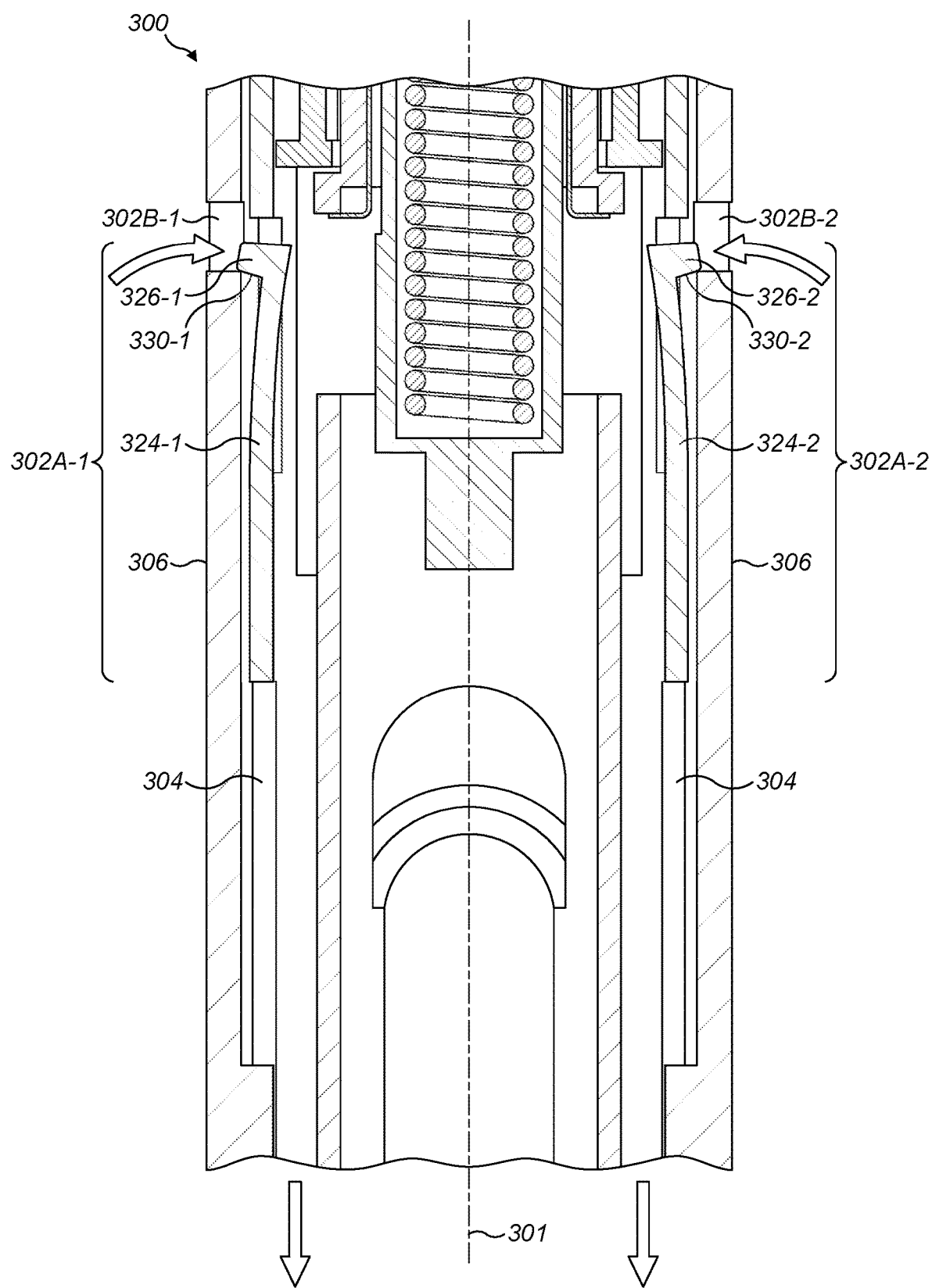

FIG. 3E shows an example of deactivation of the hold detent mechanism of the injection device in which the user starts to release the user holding force to enable the needle shroud 304 to extend out of the injection device body or outer casing 306, e.g., during removal of the needle from the body of the subject after an injection has occurred and the required dosage of medicament has been delivered. As the needle shroud 304 starts to extend out of the outer casing 306 of the injection device 300, for example under the control spring force of the control spring, the ramped surface or contact faces 330-1 and 330-2 of the first hold detent features 302A-1 and 302A-2, respectively, are guided against the edge of the corresponding slots to transform the control spring force 318 into a radial force that biases or works to inwardly flex the flexible arms (e.g., clips) 324-1 and 324-2 of the first detent features 302A-1 and 302A-2, respectively, towards the longitudinal axis 301 of the injection device 300. This enables the needle shroud 304 to extend and extract outwards from the outer casing 306. The force a user feels on removal will also be reduced by the additional friction caused by the male components 326-1 and 326-2 being biased against the inner surface of the outer casing 306 as the needle shroud 304 moves in the distal direction parallel to the longitudinal axis 301 during extraction of the need shroud 304 to a final position that is substantially similar or the same as the initial position of the needle shroud 304 as shown in FIG. 3F.

Figure 3F:
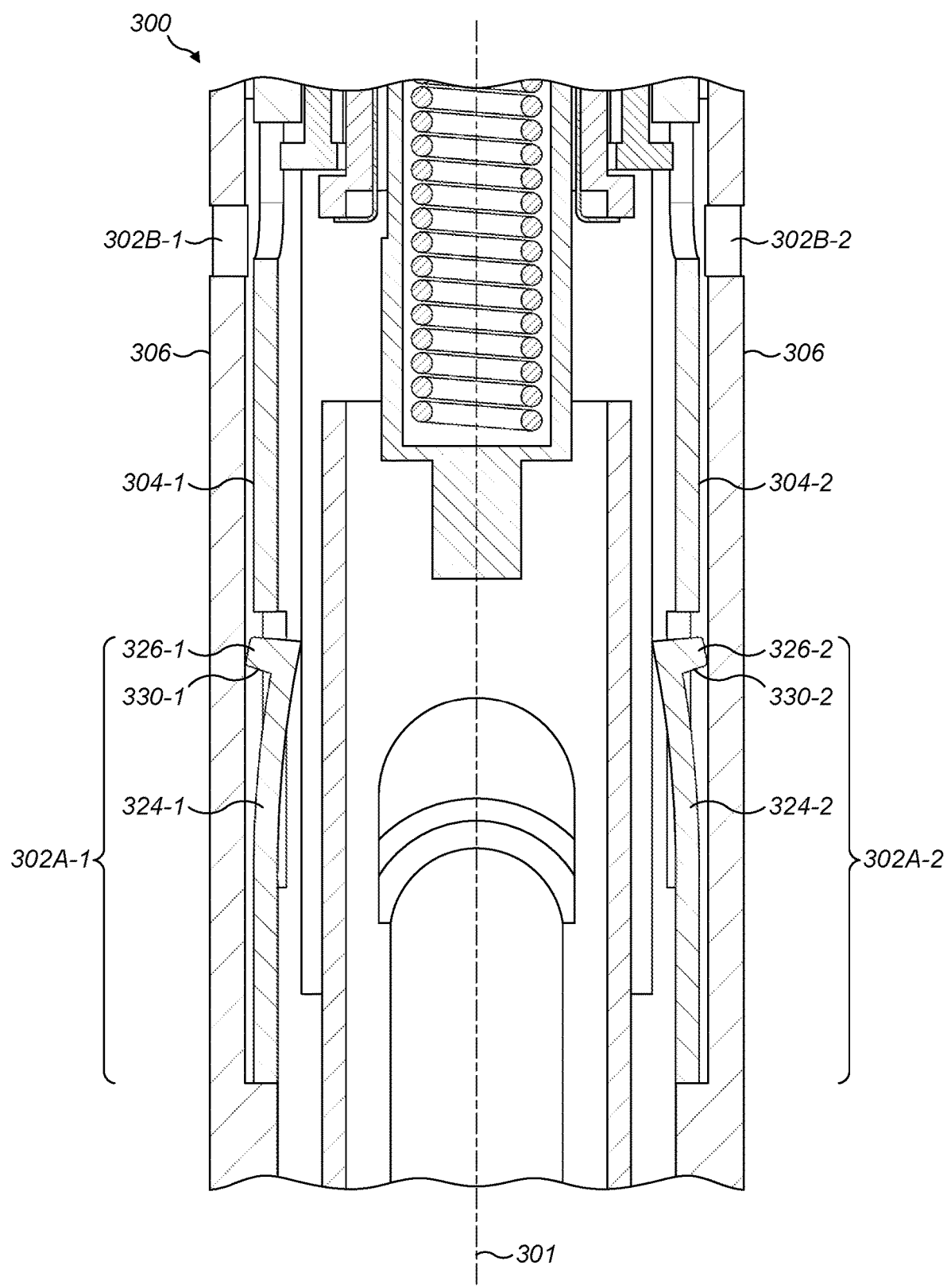

FIG. 3F shows an example of a pre-final or final configuration of the hold detent mechanism and needle shroud 304, e.g., the configuration as the needle shroud extends from the injection device body or outer casing 306 prior to reaching a final position or after the needle shroud 304 has extended fully from the injection device body or outer casing 306 after retraction to the final position. In the pre-final configuration, but after the hold detent mechanism has deactivated, the needle shroud 304 extends out of the outer casing 306 of the injection device 300 under the control spring force of the control spring, where the flexible arms (e.g., clips) 324-1 and 324-2 of the first detent features 302A-1 and 302A-2 are inwardly biased. The force a user feels on removal will also be reduced by the additional friction caused by the male components 326-1 and 326-2 being biased against the inner surface of the outer casing 306 as the needle shroud 304 moves in the distal direction parallel to the longitudinal axis 301 to extend out of the outer casing 306 to the final position that is substantially similar or the same as the initial position of the needle shroud 304. In the final position configuration, the needle shroud 304 may be locked (e.g., a non-return surface or latch is activated) to prevent further retraction of the needle shroud 304 into the injection device and thus exposure of the used needle. This may be achieved by a locking mechanism that locks the needle shroud 304 when it reaches the final position, which is substantially similar or the same as the initial position as described in FIGS. 1 and/or 3A.

Figure 4:
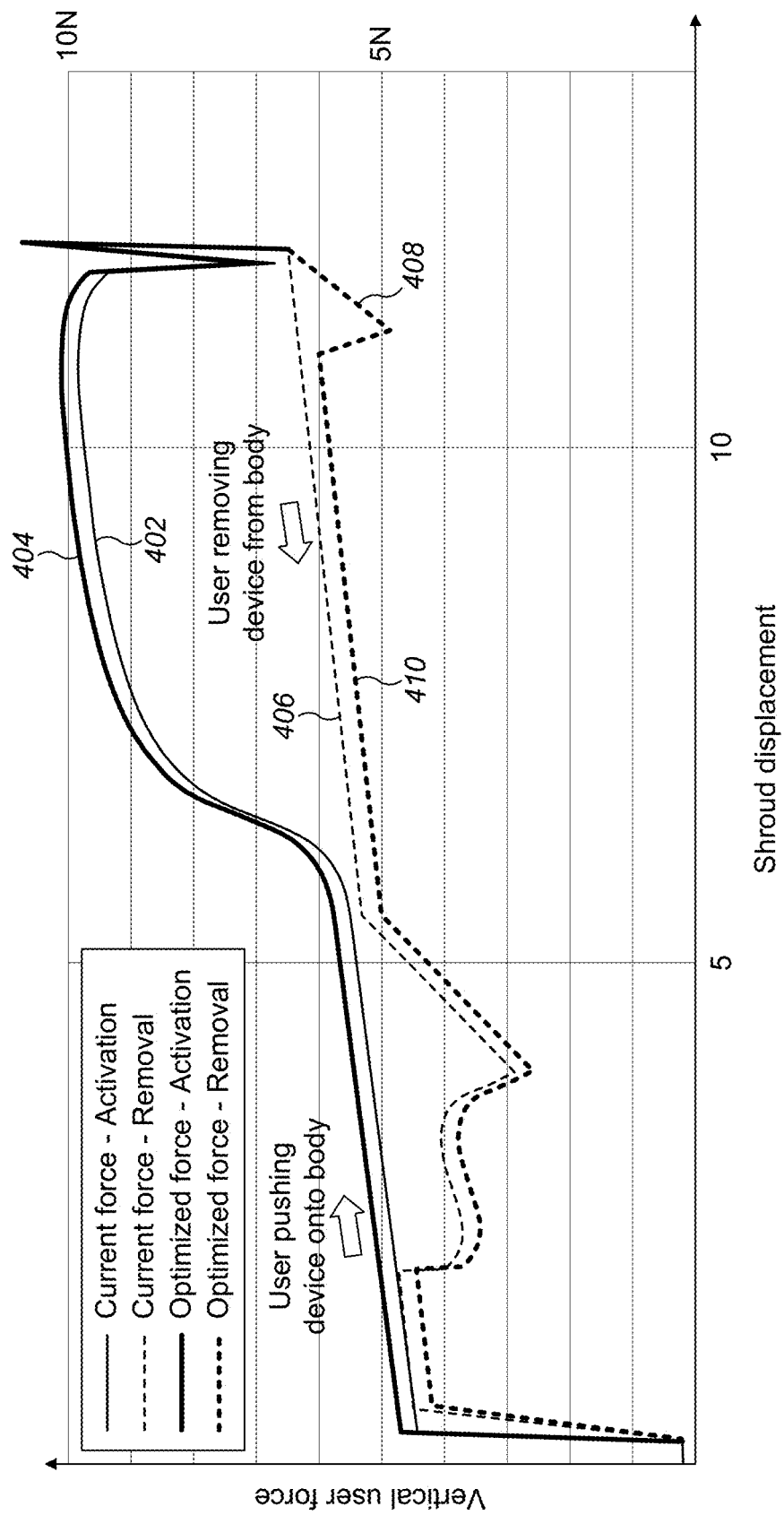
FIG. 4 shows an example comparison of force profiles of an injection device during use.

FIG. 4 shows an example comparison of force profiles of an injection device during use. The graph shows a magnitude of a vertical force applied (in Newtons, N) by a user as a function of needle shroud displacement (in mm) during insertion and removal of the device from a subject's body for both a first injection device (e.g., using a first needle locking mechanism) and a device using a collar as described herein.

The first trace 402 shows the force profile of the activation force of a first device without a hold detent mechanism when a user is pushing the device onto a subject's body. The second trace 404 shows the force profile of the activation force of an injection device 300 according to embodiments of the present disclosure as described with reference to any of FIGS. 3A to 3F, when the user is pushing the device onto a subject's body. The third trace 406 shows the force profile of the first device when a user is removing the device from a subject's body. The fourth trace 408 and 410 shows the force profile of an injection device 300 according to embodiments of the present disclosure, when the user is removing the device from a subject's body.

As can be seen, the force profile of the second trace 404 is slightly increased meaning the user requires an increased activation force for retracting the needle shroud of the injection device 300 due to friction of the first hold detent features against the outer casing of the injection device 300 caused by biassing of the flexible arms of the first hold detent features. However, more importantly, trace 408 shows a reduction in the hold force required by the user when the hold detent mechanism of the injection device 300 is activated in the hold position as described with reference to FIGS. 3A to 3F. This reduction in hold force by the user improves the ability of the user to ensure the correct dosage of the medicament to be delivered while minimizing discomfort and/or pain to the subject. The hold detent mechanism reduces the force that a user has to apply to maintain the needle shroud of the injection device 300 in the hold position by approximately 1.5 N compared with the first device (e.g., compare traces 406 and 408).

On device removal, the removal force profile 410 for the device utilizing embodiments described herein also differs from the first device removal profile 406 in that there is a constant reduction in force required by the user in the range of approximately 0.5 N. This reduction in force is caused by the additional friction of the first hold detent features against the outer casing of the injection device 300 caused by biassing of the flexible arms of the first hold detent features which supports a proportion of the control spring force as described with reference to FIGS. 3A to 3F. This reduction in remove force further improves user control of the device during removal and reduces or minimizes discomfort and/or pain to the subject.

Although the hold detent mechanisms and first hold detent feature are described herein as being a flexible arm or clip, this is by way of example only and the disclosure is not so limited, it is to be appreciated by the skilled person that modifications may be made to the hold detent mechanism and/or first hold detent feature such that they are suitable for activating the hold detent mechanism for creating a hold force when the needle shroud is at the hold position and deactivated when the medicament is delivered and needle shroud extends to substantially the initial position, or a final position in which part of the needle shroud extends out of the outer casing of the injection device and encloses the needle. A locking mechanism, e.g., non-return surface etc., may be used to ensure the needle shroud is prevented from retracting and exposing the used needle of the used injection device. In some embodiments or modifications, the resilient and/or flexible arm or clip of the hold detent mechanism and/or the first hold detent feature may include, without limitation, for example a resilient/flexible partial cut-out or resilient "flap" on the shroud with a corresponding second hold detent feature for engaging or interacting with the partial cut-out or flap (e.g., the second hold detent feature may be a recess into which a male component on the partial cut-out or flap may engage with to create the hold force as described herein). In other embodiments or modifications, the resilient and/or flexible arm or clip of the first hold detent feature may be a spring loaded flap or arm that snap-fits to the needle shroud, where the spring loaded flap is biased by spring for engaging with a second hold detent feature (e.g., recess or partial recess) to create the hold detent force, which may be overcome by the control spring force when the user releases the user hold force. Alternatively, or additionally, the flexible arm and/or clip may be, without limitation, for example a flap angled outwards from the needle shroud for engaging with a recess, hole or similar feature in the outer casing/collar that creates the hold detent force and acts as a hold detent. The flap feature may be further configured to slide smoothly against the surface of the outer casing and/or collar in both directions of travel to the hold position and from the hold position to substantially the initial position and/or a final position of the needle shroud.

Alternatively or additionally, rather than flexible arms or clips, further modification to the hold detent mechanism may include configuring the first and second hold detent features to be resistive features that activate when the needle shroud is in the hold position to add a resistive force that creates a hold detent force for reducing the user hold force and counteracting the control spring force in the hold position, but when the user releases the hold force the resistive features are configured to release the hold detent force via the control spring force. For example, the resistive features of the first and second hold detent features may be a high friction interface positioned on the needle shroud and/or positioned on the inner surface of the outer casing such that, when they meet during retraction of the needle shroud, they add a resistive force and create the hold detent force, but which may be overcome by the control spring force when the user releases the user hold force. The high friction interface may be a material interface with a high friction in the hold position used to create the hold detent force. The material interface may be, without limitation, for example a crush rub interface in which the inherent stiffness of the material, which may be part of the needle shroud and/or injection device body or outer casing that provides a contact force resulting in a friction force, which creates the hold detent force and assists in reducing the user hold force against the control spring force when the needle shroud and/or injection device is being maintained in the hold position. When the user hold force is released after the medicament has been delivered to the subject, then the control spring force overcomes the contact force/friction force caused by the material interface and the needle shroud extends to substantially its initial position or a final position in which the needle shroud extends from the outer casing of the injection device and encloses the used needle. The needle shroud may be locked using a locking mechanism that prevents the needle shroud from retracting to expose the used needle. In some embodiments, the locking mechanism may also be a high friction interface that is configured to retain the needle shroud in the final position. Alternatively, or additionally, the high friction interface may be based on smaller-scale elastic deformation of the material of the outer casing or needle shroud, e.g., a small domed or convex feature on the needle shroud or outer casing which can "bump-off" and/or engage with a concavity feature on the opposing side of the outer casing or needle shroud, respectively.

Figure 5:
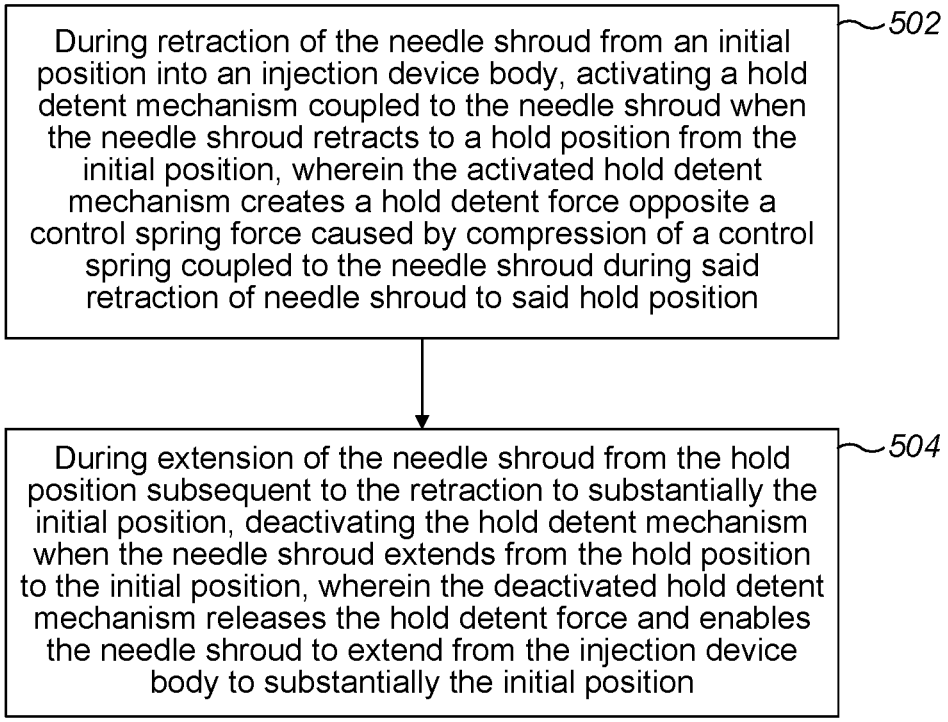
FIG. 5 shows a flow diagram of an example method of operating a hold detent mechanism for holding a needle shroud of an injection device.

FIG. 5 shows a flow diagram of an example method of operating a needle shroud of an injection device with a hold detent mechanism. The method corresponds to the operations described in relation to FIGS. 2A to 3F.

At operation 502, during retraction of the needle shroud from an initial position into an injection device body, activating a hold detent mechanism coupled to the needle shroud when the needle shroud retracts to a hold position from the initial position. The activated hold detent mechanism is configured to create a hold detent force opposite a control spring force caused by compression of a control spring coupled to the needle shroud during said retraction of needle shroud to said hold position.

At operation 504, during extension of the needle shroud from the hold position subsequent to the retraction to substantially the initial position, deactivating the hold detent mechanism when the needle shroud extends from the hold position to the initial position, wherein the deactivated hold detent mechanism releases the hold detent force and enables the needle shroud to extend from the injection device body to substantially the initial position.

In some examples, subsequent to the extension of the needle shroud, further retraction of the needle shroud into the injection device body is prevented using a non-return surface on the collar. The non-return surface may comprise an angled edge that urges the collar in the same rotation direction as the first and second angled portions, i.e., prevents the collar rotating back to the hold or initial positions.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab') 2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full-length antibody polypeptide, although the term is not limited to such cleaved fragments. Antibody fragments that are useful in the present invention include, for example, Fab fragments, F(ab') 2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing
104—reservoir
106—plunger
108—collar
110—cap
112—longitudinal axis
114—rear casing
116—needle
118—needle shroud/sleeve/cover
120—control spring
122—drive spring
124—stopper
126—distal end
128—proximal end
200—injection device
202—hold detent mechanism
202A—first hold detent feature
202B—second hold detent feature
204—needle shroud/sleeve/cover
206—outer casing/housing
208—control spring
210—reservoir
212—needle
214—subject
216—hold force
218—control spring force
220—hold detent force
222—hold detent mechanism
224—flexible arm
226—male component of first hold detent feature
228—first ramped surface of male component 226
230—second ramped surface of male component 226
231—tipped surface or point of male component 226
232—hold detent mechanism
234—hold detent mechanism
236—first ramped surface of male component
238—second ramped surface of male component
237—tipped surface or point of male component
240—injection device
242—hold detent mechanism
242A—first hold detent feature
242B—second hold detent feature
244—collar
246—hold force
248—control spring force
250—hold detent force
252—hold detent mechanism
254—hold detent mechanism
256—hold detent mechanism
300—injection device
301—longitudinal axis of the injection device 300
302—hold detent mechanism
302A-1/2—first hold detent feature
302B-1/2—second hold detent feature
304—needle shroud/sleeve/cover
306—outer casing/housing
316—user activation force
317—user holding force
318—control spring force
320—hold detent force
324-1/2—flexible arm/clip
326-1/2—male component of first hold detent feature 302A-1/2
330-1/2—ramp surface of first hold detent feature 302A-1/2
402—Force profile of first device during insertion
404—Force profile of embodiments during insertion
406—Force profile of first device during removal
408—Force profile of embodiments during hold
410—Force profile of embodiments during removal

The invention claimed is:

1. An injection device comprising:
an injection device body;
a needle shroud retractable into the injection device body;
a control spring coupled to the needle shroud and biased to cause the needle shroud to be at least partially extended from the injection device body in an initial position; and
a hold detent mechanism coupled to at least the needle shroud, wherein the hold detent mechanism is configured to:
activate, when the needle shroud is retracted from the initial position into the injection device body to a hold position, to create a hold detent force opposite a control spring force caused by compression of the control spring during said retraction of needle shroud to said hold position; and
deactivate, when the needle shroud is extracted from the hold position subsequent to the retraction, to release the hold detent force and enable the needle shroud to extend from the injection device body to substantially the initial position; and
a collar within the injection device body and rotatably configured for guiding said needle shroud between the initial position and the hold position;
a plunger and biasing means for biasing the plunger towards a distal end of the injection device,
wherein when the needle shroud is in the initial position, the plunger is retained by a combination of a rear casing of the injection device and the collar preventing the biasing means from displacing the plunger in a distal direction, and on activation of the injection device, the collar rotates and guides the needle shroud to the holding position and causing, when the needle shroud is in the holding position, the biasing means to move the plunger in the distal direction of the injection device.

2. The injection device of claim 1, wherein the hold detent mechanism comprises a first hold detent feature coupled to the needle shroud, which, when activated, interacts with a second hold detent feature on the injection device body for creating the hold detent force.

3. The injection device of claim 1, wherein the hold detent mechanism comprises a first hold detent feature coupled to the needle shroud, which, when activated, interacts with a second hold detent feature on the collar for creating the hold detent force.

4. The injection device of claim 2, wherein the first hold detent feature comprises at least one of:
    a flexible arm;
    a resilient clip;
    a high friction interface; or
    partial cut-out or flap on the needle shroud.

5. The injection device of claim 2, wherein the first hold detent feature comprises a male feature, and the second hold detent feature comprises at least one of:
    a recess for mating with said male feature of the first hold detent feature;
    a partial recess for mating with said male feature of the first hold detent feature;
    a male feature configured to interact and couple with the male feature of the first hold detent feature; or
    a high friction interface.

6. The injection device of claim 5, wherein;
    the male feature of the first hold detent feature comprises at least one ramped contact face configured for flexing a portion of the first hold detent feature radially away from the injection device body or the collar when the needle shroud is in the initial position and/or prior retracting to the hold position;
    when the needle shroud is retracted to the hold position, the hold detent mechanism activates by the at least one ramped contact face of the male feature of the first hold detent feature interacting with the second hold detent feature of the injection device body or the collar causing the portion of the first hold detent feature to radially flex towards the injection device body or the collar, respectively, and create the hold detent force opposite the control spring force; and
    when the needle shroud is extracted from the hold position subsequent to the retraction, the hold detent mechanism is deactivated by the at least one ramped contact face of the male feature of the first hold detent feature interacting with the second hold detent feature to radially flex the portion of the first hold detent feature away from the injection device body or the collar, respectively, enabling the control spring force to extract the needle shroud to substantially the initial position.

7. The injection device of claim 2, wherein the first hold detent feature is coupled to the needle shroud by a snap fit.

8. The injection device of claim 2, wherein the first hold detent feature is integral to the needle shroud and formed by a resilient partial cut-out of the needle shroud.

9. The injection device of claim 1, wherein the hold detent force of the hold detent mechanism at least partially supports the needle shroud against the control spring force rather than an entirety of the control spring force being fully transferred to a user when the injection device is in the hold position.

10. The injection device of claim 1, wherein the control spring is a compression spring configured to bias the needle shroud towards an extended position.

11. The injection device of claim 1, wherein the injection device further comprises a needle, and wherein the needle shroud is arranged to shroud the needle when in an extended position.

12. The injection device of claim 11, wherein the injection device further comprises a reservoir containing a medicament, the reservoir coupled to the plunger via a stopper at a distal portion of the reservoir and the reservoir coupled to the needle at a proximal end of the reservoir, and wherein, when the needle shroud moves into the hold position, the biasing means moves the plunger to displace the stopper in the distal direction causing the medicament stored in the reservoir to be expelled from the injection device via the needle.

13. The injection device of claim 1, further comprising at least two hold detent mechanisms equally spaced around a circumference of the needle shroud.

14. A hold detent mechanism for an injection device, the hold detent mechanism comprising:
    a first hold detent feature coupled to a needle shroud, wherein the needle shroud is retractable into an injection device body and coupled to a control spring, the control spring biased to cause the needle shroud to be at least partially extended from the injection device body in an initial position, the first hold detent feature comprising a male feature;
    a second hold detent feature comprises at least one of (i) a recess for mating with said male feature of the first hold detent feature, (ii) a partial recess for mating with said male feature of the first hold detent feature, (iii) a male feature configured to interact and couple with the male feature of the first hold detent feature, or (iv) a high friction interface,
    wherein the hold detent mechanism is configured to:
        activate the first hold detent feature, when the needle shroud is retracted from the initial position into the injection device body to a hold position, to create a hold detent force opposite a control spring force caused by compression of the control spring during said retraction of needle shroud to said hold position; and
        deactivate the first hold detent feature, when the needle shroud is extracted from the hold position subsequent to the retraction, to release the hold detent force and enable the needle shroud to extend from the injection device body to substantially the initial position,
    wherein the male feature of the first hold detent feature comprises at least one ramped contact face configured for flexing a portion of the first hold detent feature radially away from the injection device body when the needle shroud is in the initial position and/or prior retracting to the hold position,
    wherein when the needle shroud is retracted to the hold position, the first hold detent feature of the hold detent mechanism activates by the at least one ramped contact face of the male feature of the first hold detent feature interacting with the second hold detent feature of the injection device body causing the portion of the first hold detent feature to radially flex towards the injection device body and create the hold detent force opposite the control spring force, and
    wherein when the needle shroud is extracted from the hold position subsequent to the retraction, the first hold detent feature of the hold detent mechanism is deactivated by the at least one ramped contact face of the male feature of the first hold detent feature interacting with the second hold detent feature to radially flex the portion of the first hold detent feature away from the injection device body enabling the control spring force to extract the needle shroud to substantially the initial position.

15. The hold detent mechanism of claim 14, wherein the second hold detent feature is on the injection device body.

16. The hold detent mechanism of claim 14, wherein the injection device further comprises a collar within the injection device body and configured for guiding said needle shroud between the initial position and the hold position.

17. The hold detent mechanism of claim 14, wherein the first hold detent feature comprises at least one of:
   a flexible arm;
   a resilient clip;
   a high friction interface; or
   partial cut-out or flap on the needle shroud.

18. The hold detent mechanism of claim 14, wherein the first hold detent feature is coupled to the needle shroud by a snap fit.

19. The hold detent mechanism of claim 14, wherein the first hold detent feature is integral to the needle shroud and formed by a resilient partial cut-out of the needle shroud.

20. The hold detent mechanism of claim 14, wherein the hold detent force of the hold detent mechanism at least partially supports the needle shroud against the control spring force rather than an entirety of the control spring force being fully transferred to a user when the injection device is in the hold position.

21. The hold detent mechanism of claim 14, wherein the control spring is a compression spring configured to bias the needle shroud towards an extended position.

22. The hold detent mechanism of claim 14, wherein the first hold detent feature comprises at least one of a flexible arm, a resilient clip, a high friction interface, or partial cut-out or flap.

23. A hold detent mechanism for an injection device, the hold detent mechanism comprising:
   a first hold detent feature coupled to a needle shroud, wherein the needle shroud is retractable into an injection device body and coupled to a control spring, the control spring biased to cause the needle shroud to be at least partially extended from the injection device body in an initial position, the first hold detent feature comprising a male feature;
   wherein the hold detent mechanism is configured to:
      activate the first hold detent feature, when the needle shroud is retracted from the initial position into the injection device body to a hold position, to create a hold detent force opposite a control spring force caused by compression of the control spring during said retraction of needle shroud to said hold position; and
      deactivate the first hold detent feature, when the needle shroud is extracted from the hold position subsequent to the retraction, to release the hold detent force and enable the needle shroud to extend from the injection device body to substantially the initial position; and
   a collar within the injection device body and configured for guiding said needle shroud between the initial position and the hold position, wherein the first hold detent feature, which, when activated, interacts with a second hold detent feature on the collar for creating the hold detent force, the second hold detent feature comprising at least one of (i) a recess for mating with said male feature of the first hold detent feature, (ii) a partial recess for mating with said male feature of the first hold detent feature, (iii) a male feature configured to interact and couple with the male feature of the first hold detent feature, or (iv) a high friction interface,
   wherein the male feature of the first hold detent feature comprises at least one ramped contact face configured for flexing a portion of the first hold detent feature radially away from the collar when the needle shroud is in the initial position and/or prior retracting to the hold position,
   wherein when the needle shroud is retracted to the hold position, the first hold detent feature of the hold detent mechanism activates by the at least one ramped contact face of the male feature of the first hold detent feature interacting with the second hold detent feature of the collar causing the portion of the first hold detent feature to radially flex towards the collar, and create the hold detent force opposite the control spring force, and
   wherein when the needle shroud is extracted from the hold position subsequent to the retraction, the first hold detent feature of the hold detent mechanism is deactivated by the at least one ramped contact face of the male feature of the first hold detent feature interacting with the second hold detent feature to radially flex the portion of the first hold detent feature away from the collar enabling the control spring force to extract the needle shroud to substantially the initial position.

24. The hold detent mechanism of claim 23, wherein the first hold detent feature is coupled to the needle shroud by a snap fit.

25. The hold detent mechanism of claim 23, wherein the first hold detent feature is integral to the needle shroud and formed by a resilient partial cut-out of the needle shroud.

26. The hold detent mechanism of claim 23, wherein the hold detent force of the hold detent mechanism at least partially supports the needle shroud against the control spring force rather than an entirety of the control spring force being fully transferred to a user when the injection device is in the hold position.

27. An injection device comprising:
   an injection device body;
   a needle shroud retractable into the injection device body;
   a control spring coupled to the needle shroud and biased to cause the needle shroud to be at least partially extended from the injection device body in an initial position; and
   a hold detent mechanism coupled to at least the needle shroud, wherein the hold detent mechanism is configured to:
      activate, when the needle shroud is retracted from the initial position into the injection device body to a hold position, to create a hold detent force opposite a control spring force caused by compression of the control spring during said retraction of needle shroud to said hold position; and
      deactivate, when the needle shroud is extracted from the hold position subsequent to the retraction, to release the hold detent force and enable the needle shroud to extend from the injection device body to substantially the initial position,
   wherein the hold detent mechanism comprises a first hold detent feature coupled to the needle shroud, which, when activated, interacts with a second hold detent feature on the injection device body for creating the hold detent force, wherein the first hold detent feature comprises a male feature, and the second hold detent feature comprises at least one of (i) a recess for mating with said male feature of the first hold detent feature, (ii) a partial recess for mating with said male feature of the first hold detent feature, (iii) a male feature configured to interact and couple with the male feature of the first hold detent feature, or (iv) a high friction interface, wherein the male feature of the first hold detent feature comprises at least one ramped contact face configured for flexing a portion of the first hold detent feature radially away from the injection device body or a collar when the needle shroud is in the initial position and/or prior retracting to the hold position, when the needle shroud is retracted to the hold position, the hold detent mechanism activates by the at least one ramped contact face of the male feature of the first hold detent feature interacting with the second hold detent feature of the injection device body or the collar causing the portion of the first hold detent feature to radially flex towards the injection device body or the collar, respectively, and create the hold detent force opposite the control spring force, and when the needle shroud is extracted from the hold position subsequent to the retraction, the hold detent mechanism is deactivated by the at least one ramped contact face of the male feature of the first hold detent feature interacting with the second hold detent feature to radially flex the portion of the first hold detent feature away from the injection device body or the collar, respectively, enabling the control spring force to extract the needle shroud to substantially the initial position.

* * * * *